US008709452B2

(12) United States Patent
Varghese et al.

(10) Patent No.: US 8,709,452 B2
(45) Date of Patent: Apr. 29, 2014

(54) SYNTHETIC BONE GRAFTS

(75) Inventors: Shyni Varghese, San Diego, CA (US);
Ameya Phadke, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/549,045

(22) Filed: Jul. 13, 2012

(65) Prior Publication Data
US 2013/0017232 A1  Jan. 17, 2013

Related U.S. Application Data

(60) Provisional application No. 61/508,185, filed on Jul. 15, 2011.

(51) Int. Cl.
*A61K 9/00* (2006.01)
*A01N 63/00* (2006.01)
*A61K 47/32* (2006.01)
*A61K 47/00* (2006.01)

(52) U.S. Cl.
USPC .... 424/400; 424/93.7; 514/772.4; 514/772.6; 514/781; 514/788

(58) Field of Classification Search
None
See application file for complete search history.

(56) References Cited

U.S. PATENT DOCUMENTS

2007/0098799 A1* 5/2007 Zhang et al. .................. 424/486

OTHER PUBLICATIONS

Ayala et al. ("Engineering the cell-material interface for controlling stem cell adhesion, migration and differentiation", Biomaterials, 32 (2011) 3700-3711.*
Phadke et al. ("Templated Mineralization of Synthetic Hydrogels for Bone-Like Composite Materials: Role of Matrix Hydrophobicity", Biomacromolecules, 2010, 11, 2060-2068.*

* cited by examiner

*Primary Examiner* — Aradhana Sasan
(74) *Attorney, Agent, or Firm* — Joseph R. Baker, Jr.; Gavrilovich, Dodd & Lindsey LLP

(57) ABSTRACT

The disclosure provides bone-mimetic mineral/polymer composite materials useful for formation of artificial bone grafts and for bone tissue engineering. The disclosure provides a hydrogels, cryogels and macroporous compositions modified with varying lengths of anionic pendant side chains ($CH_2=CHCONH(CH_2)_n COOH$, where n=1 to 12).

33 Claims, 21 Drawing Sheets

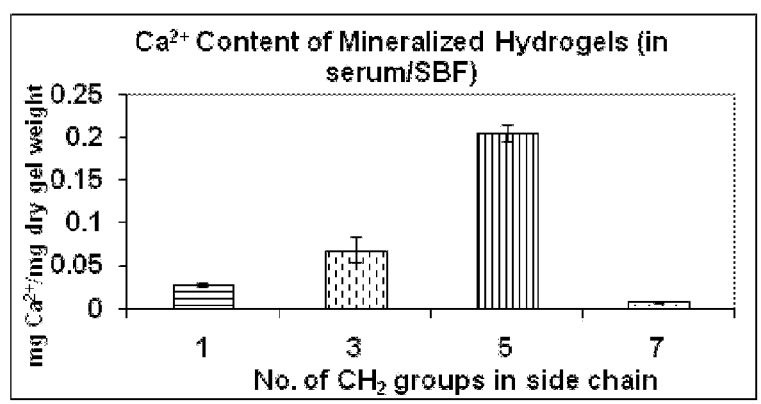
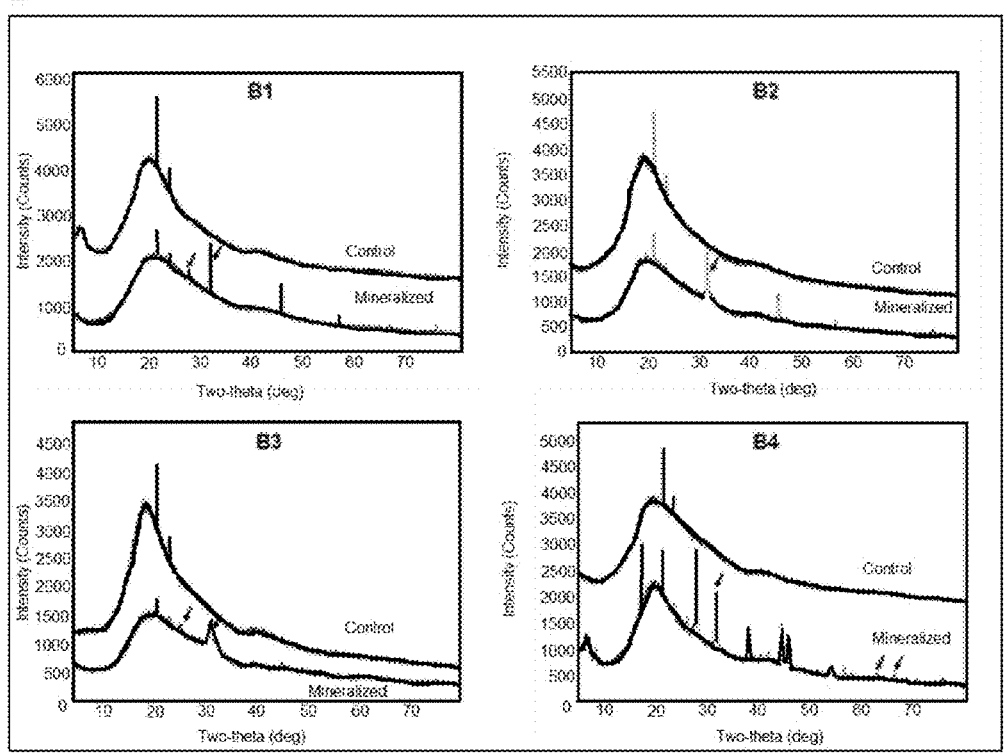
FIGURE 2A-B

FIGURE 11A-G

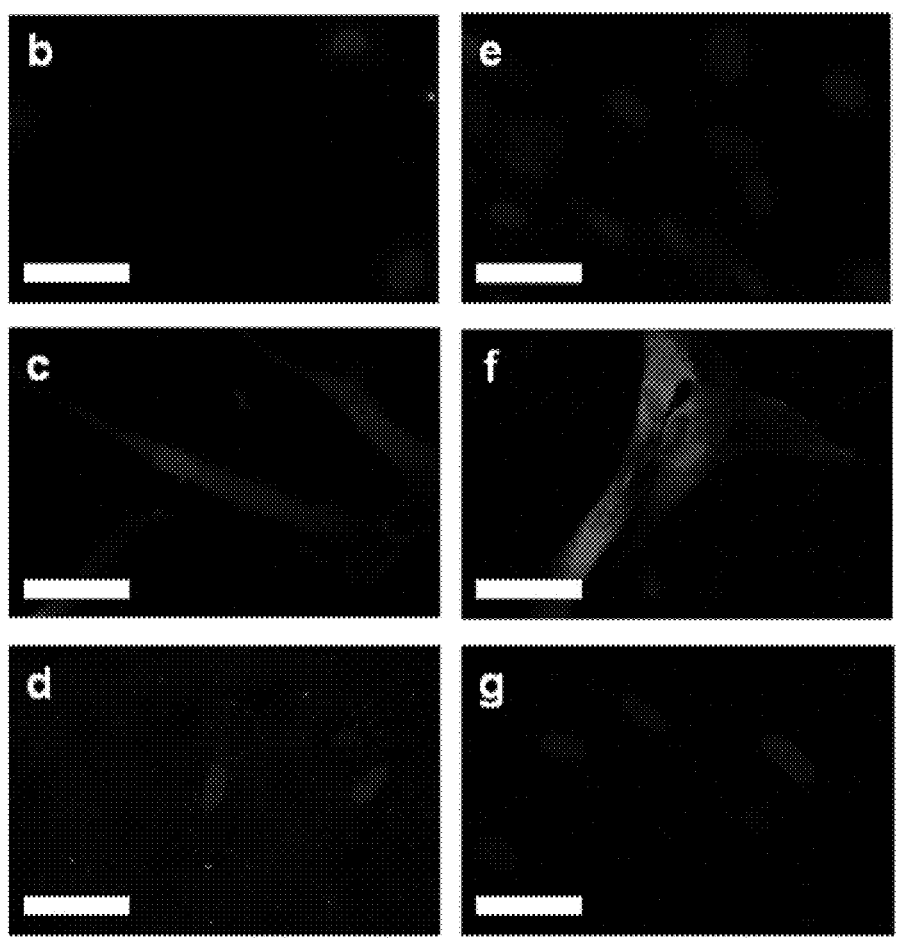
FIGURE 13B-G

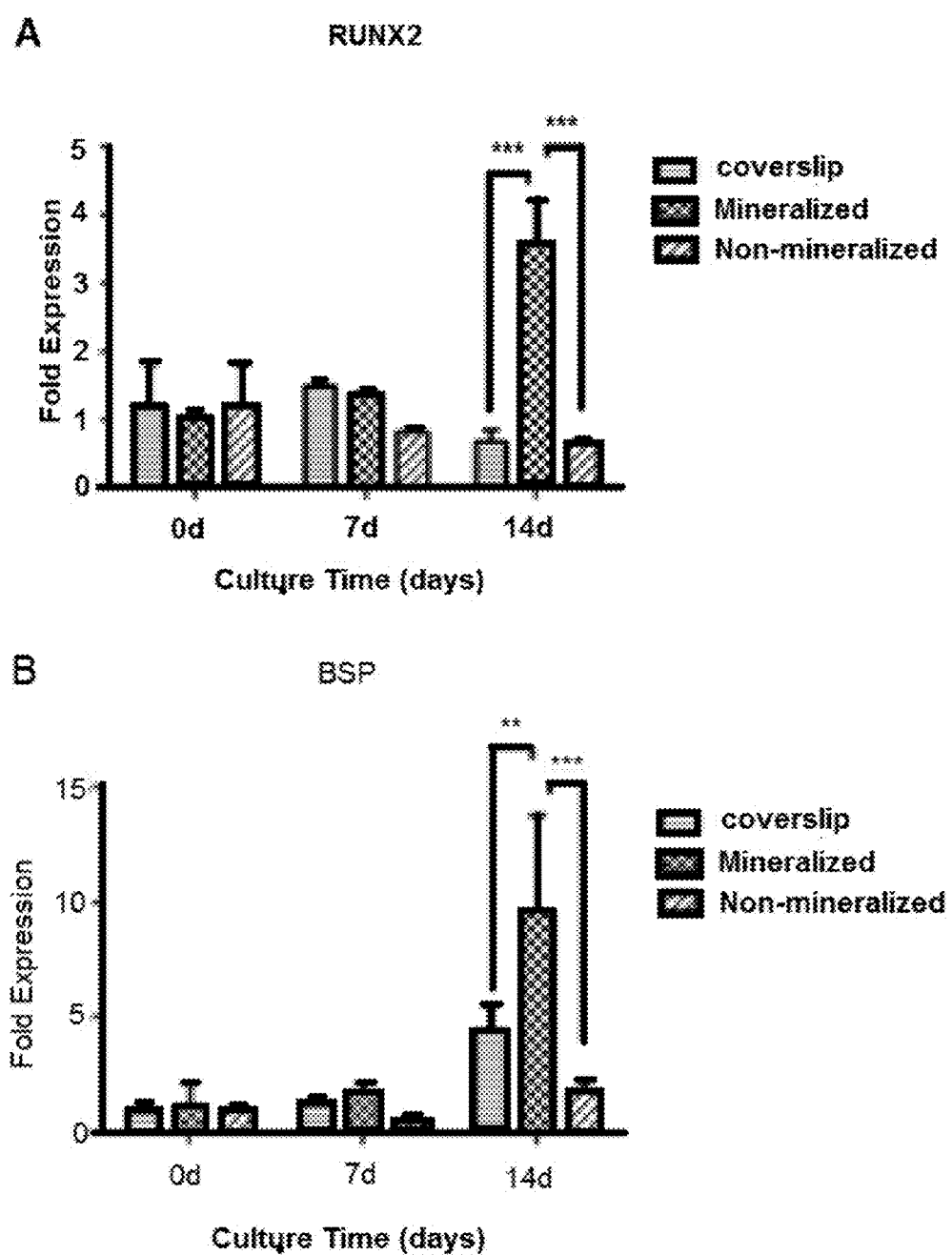
FIGURE 14A-B

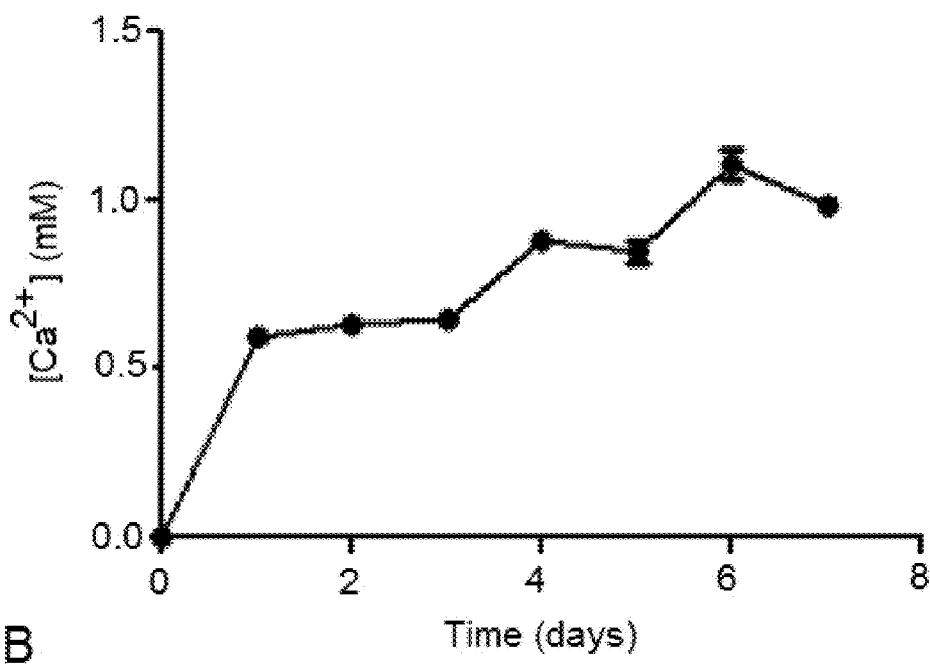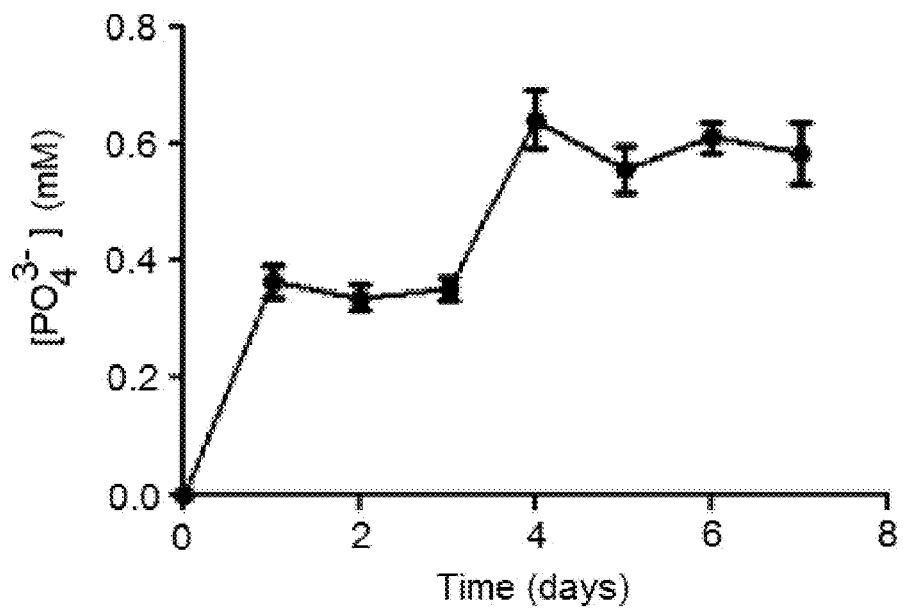
FIGURE 15A-B

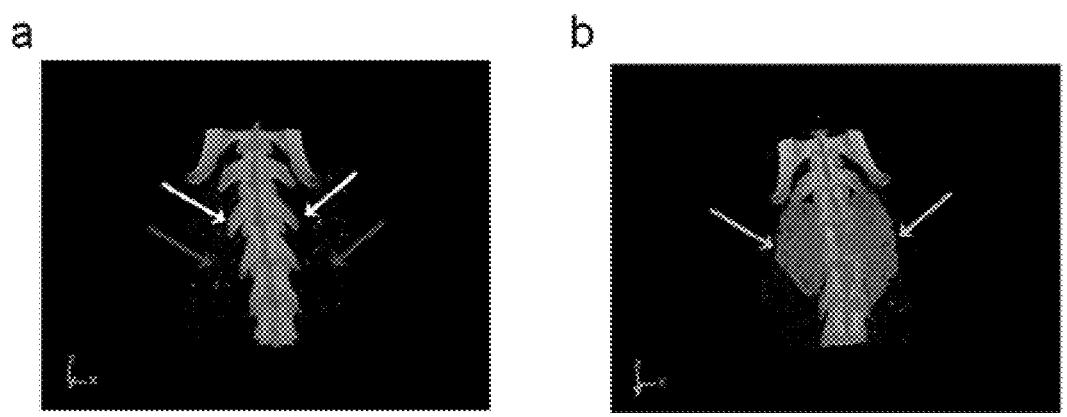
FIGURE 25A-B

SYNTHETIC BONE GRAFTS

CROSS REFERENCE TO RELATED APPLICATIONS

This application claims priority under 35 U.S.C. §119 from Provisional Application Ser. No. 61/508,185, filed Jul. 15, 2011, the disclosure of which is incorporated herein by reference.

TECHNICAL FIELD

The disclosure relates to biocompatible materials useful for tissue formation and stem cell differentiation.

BACKGROUND

Current bone graft materials include (i) ceramic powders, (ii) combinations of proteins and minerals, (iii) autologous, allografts and xenografts bone grafts. Xenografts and allografts often suffer from rejection due to non-immunocompatibility. The greatest limitation with autologous bone grafts is donor site morbidity, invasiveness and pain. Ceramic powders do not provide structural support and do not mimic the composite structure of bone. Compositions comprising a combination of hydroxyapatite and collagen-I do not mimic the composite structure observed in bone. Additionally, while ceramic powders and collagen-I/hydroxyapatite composites allow for bone in-growth (osteoconductivity), they do not promote the differentiation of progenitor cells into bone specific lineages (osteoinductivity).

SUMMARY

The disclosure provides a calcium phosphate (CaP)-/apatite-like mineral phase and a hydrogel polymer phase, synthesized through a biomimetic templating process and thereby effectively mimics the structure of native bone.

Polyanionic hydrogels comprising various length sidegroups terminating with a functional group such as a carboxyl group are used to bind $Ca^{2+}$ and $PO_4^{3-}$. For example, polyanionic hydrogels comprising poly(ethylene glycol)-diacrylate and N-acryloyl modified amino acids, with varying side chain length and terminal carboxyl group are synthesized. When exposed to $Ca^{2+}$ and $PO_4^{3-}$ ions in solution, the terminal carboxyl groups bind $Ca^{2+}$ and serve as nucleation sites for apatite/CaP-formation, leading to the formation of a porous mineralized bone mimetic material. By changing the side chain length, the extent of mineralization can be controlled as well as the morphology of the mineralized phase, allowing for highly controlled scaffold fabrication. Thus, one can control the amount of CaP-/apatite in the scaffold, as well as the topology of the mineral phase.

The disclosure provides a composition comprising a hydrogel modified with amino acids having an anionic pendant side chain and having the general formula $CH_2$=$CHCONH(CH_2)_n COOH$, where n=1 to 12. In one embodiment, the hydrogel comprises amino acids selected from the group consisting of: (a) $CH_2$=$CHCONH(CH_2)_n COOH$, (b) $CH_2$=$CHCONH(CH_2)_2 COOH$, (c) $CH_2$=$CHCONH(CH_2)_3 COOH$, (d) $CH_2$=$CHCONH(CH_2)_4 COOH$, and (e) any combination of (a)-(d). In another embodiment, the composition is mineralized. In yet another embodiment, the composition comprises $CH_2$=$CHCONH(CH_2)_3 COOH$. In one embodiment, the composition is seeded with cells. In yet another embodiment, the cells are stromal cells. In yet a further embodiment, the stromal cells are selected from fibroblast cells, chondrocytes, osteocytes and a combination thereof. In yet a still further embodiment, the cells are stem cells. For example, the stem cells can be mesenchymal stem cells. In other embodiments, the cells are selected from the group consisting of endothelial cells, myoblasts, cardiomyocytes, stem cells, skeletal muscle cells, smooth muscle cells, fibroblasts, a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a postnatal stem cell. In yet any of the foregoing embodiments, the hydrogel is molded. In yet any of the foregoing embodiments, the hydrogel is composed of a material selected from the group consisting of agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol) monomethacrylate, chitin, poly(hydroxyalkyl methacrylate), poly(electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester crosslinked polyglucans, and derivatives and combinations thereof. In any of the foregoing embodiments, the composition can further comprising serum proteins.

The disclosure also provides macroporous composition comprising amino acids having an anionic pendant side chain and having the general formula $CH_2$=$CHCONH(CH_2)_n COOH$, where n=1 to 12 (e.g., 1 to 8). In one embodiment, the macroporous composition comprises amino acids having a general formula selected from the group consisting of: (a) $CH_2$=$CHCONH(CH_2)COOH$, (b) $CH_2$=$CHCONH(CH_2)_2 COOH$, (c) $CH_2$=$CHCONH(CH_2)_3 COOH$, (d) $CH_2$=$CHCONH(CH_2)_4 COOH$, and (e) any combination of (a)-(d). In yet another embodiment, the composition is mineralized. In yet another embodiment, the composition comprises $CH_2$=$CHCONH(CH_2)_3 COOH$. In another embodiment, the macroporous compositions comprises a lamellar columnar structure with a pore size of approximately 50-60 μm in the dried state (corresponding to ~100-150 μm in the swollen state) and comprising an acryloyl amino acid selected from the group consisting of $CH_2$=$CHCONH(CH_2) COOH$, $CH_2$=$CHCONH(CH_2)_2 COOH$, $CH_2$=$CHCONH(CH_2)_3 COOH$, $CH_2$=$CHCONH(CH_2)_4 COOH$, and any combination thereof. In another embodiment, the macroporous compositions comprises randomly oriented, interconnected cellular pores measuring approximately 20-30 μm in diameter in the dried state (corresponding to 50-60 µm in the swollen state) and comprising an acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof. In one embodiment, the composition comprises spherical interconnected pores 200-300 µm in diameter and comprising an acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof. In any of the foregoing embodiments, the composition can be seeded with cells such as stromal cells selected from fibroblast cells, chondrocytes, osteocytes and a combination thereof or stem cells such as mesenchymal stem cells. In one embodiment, the cells are selected from the group consisting of endothelial cells, myoblasts, cardiomyocytes, stem cells, skeletal muscle cells, smooth muscle cells, fibroblasts, a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a postnatal stem cell. In any of the foregoing embodiment, the macroporous composition can be molded. In another embodiment, the macroporous composition is derived from a material selected from the group consisting of agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol) monomethacrylate, chitin, poly(hydroxyalkyl methacrylate), poly(electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester cross-linked polyglucans, and derivatives and combinations thereof. In another embodiment, the macroporous composition is formed through cryogelation or through PMMA-microsphere leaching, gas-foaming or salt leaching.

The disclosure also provides methods of using any of the foregoing hydrogels, cryogels, or macroporous compositions for the treatment of bone disease or disorders of for growing bone comprising implanting the hydrogel, cryogel, macroporous composition either with or without cells at the site of desired bone formation.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-B shows observed data of a composition of the disclosure. (A) Extent of mineralization (measured as the total $Ca^{2+}$ content in the mineralized hydrogels, normalized to dry gel weight) for hydrogels containing amino acid monomers with varying pendant side chain length, mineralized by immersion in serum supplemented SBF. Error bars represent standard deviation. (B) X-ray diffraction spectra for hydrogels containing amino acid monomers with (B1) one methylene group; A2AGA (B2) three methylene groups; A4ABA (B3) five methylene groups: A6ACA and (B4) seven methylene groups; A8ACA, respectively, mineralized by immersion in serum supplemented SBF, with a control sample of each hydrogel (non-mineralized) containing the respective amino acid monomer for comparison. Arrows indicate hydroxyapatite peaks (PDF-04-010-6312 in PDF-4+ database).

FIGS. 13A-G shows immunostaining of osteocalcin in hMSCs. (A) Production of the bone marker alkaline phosphatase (ALP) at 2 weeks on coverslips, mineralized and non-mineralized hydrogels. Error bars indicate standard error of the mean, asterisks indicate statistical significance (n=3; *: p<0.05). (B-G) Staining for the bone marker osteocalcin at 2 weeks on (B) coverslips, (C) mineralized hydrogels and (D) non mineralized hydrogels, and at 3 weeks on (E) coverslips (F) mineralized hydrogels and (G) non-mineralized hydrogels. Scale bars represent 50 μm.

FIGS. 14A-C show osteogenic gene expression of hMSCs on hydrogels. Expression of bone markers (A) Runx2 (B) Bone sialoprotein (BSP) and (C) Osteocalcin (OCN) on the coverslips, mineralized hydrogels and non-mineralized hydrogels at various time points. Expression is normalized to GAPDH expression and expressed as fold change relative to day 0 expression levels. Error bars represent standard error of the mean (n=3) and asterisks represent statistical significance between groups indicated (: p<0.01, *: p<0.001).

FIGS. 15A-B show dissolution of $Ca^{2+}$ and $PO_4^{3-}$ from hydrogels. Release of (A) $Ca^{2+}$ and (B) $PO_4^{3-}$ from mineralized hydrogels in $Ca^{2+}$- and $PO_4^{3-}$-free Tris buffer (pH 7.4). The measurements over the period of 1 week suggest dissolution of the mineralized phase as well as their re-precipitation upon saturation.

FIGS. 25A-B show micro-computed tomography of bone formation during posterolateral lumbar fusion in nude rats by the synthetic bone grafts (A) immediately after implantation and (B) after 4 weeks of implantation. In (A), white arrows indicate the transverse processes, gray arrows indicate the location of the implanted grafts. In (B), the arrows indicate the new bone formed in the grafts and along the transverse processes.

DETAILED DESCRIPTION

Figure 1:
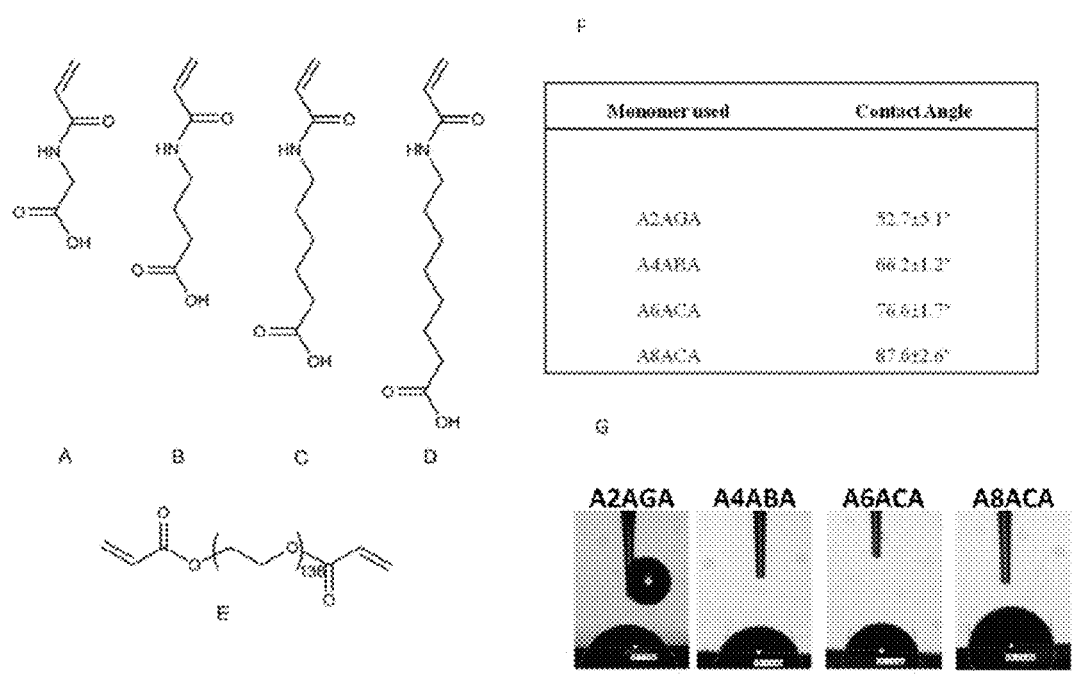
FIGS. 1A-G shows N-acryloyl amino acids with varying side chain length, namely: (A) A2AGA (B) A4ABA (C) A6ACA (D) A8ACA (E) poly(ethylene glycol) (MW: 6 kDa)-diacrylate (PEGDA-6K), used as a crosslinker in this study. (F) Shows water contact angles for hydrogels synthesized with varying side chain length and (G) shows images of water droplets on the hydrogels with varying side chain length.

As used herein and in the appended claims, the singular forms "a," "and," and "the" include plural referents unless the context clearly dictates otherwise. Thus, for example, reference to "a cell" includes a plurality of such cells and reference to "the tissue" includes reference to one or more tissues and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The term "biocompatible" is art-recognized. For example, biocompatible hydrogels include hydrogels that are neither themselves toxic to the host (e.g., an animal or human), nor degrade at a rate that produces monomeric or oligomeric subunits or other by-products at toxic concentrations in the host.

As used herein, "biodegradable" means that a hydrogel or cryogel, once implanted into a host, will begin to degrade.

The rate of biodegradation may be engineered into the hydrogel or cryogel based on the polymers used, the ratio of copolymers used, the amount of minerals, and other parameters well known to those of skill in the art.

The term "cross-linked" as used herein refers to a composition containing intermolecular cross-links and optionally intramolecular cross-links arising from the formation of covalent bonds, ionic bonds, hydrogen bonding, or any combination thereof. "Cross-linkable" refers to a component or compound that is capable of undergoing reaction to form a cross-linked composition.

"Cryogels" are a class of materials with a highly porous (macroporous) structure and having a broad variety of morphologies. Cryogels are produced using a cryotropic gelation technique.

Cryotropic gelation (cryogelation or cryostructuration) is a specific type of gel-formation which takes place as a result of cryogenic treatment of the systems potentially capable of gelation. A feature of cryogelation is compulsory crystallization of the solvent such as water. This distinguishes cryogelation from chilling-induced gelation, when the gelation takes place on decreasing temperature.

A typical feature of cryogelation is the ability to produce a system of interconnected macropores. The macropore size can be as large as a few hundred microns. The cryogels often have sponge-like morphology, which is contrary to traditional continuous monophase gels that are produced from the same precursors, but at temperatures above freezing.

Cryogels are mechanically strong which is sometimes desirable in certain applications such as wound dressing films and foams. The production of cryogels in general is well documented (Vide e.g. Kaetsu, I., Adv. Polym. Sci. 105: 81 (1993); Lozinsky, V. I. and Plieva, F. M., Enzyme Microb. Tech-No I. 23: 227-242 (1998); and Hassan, Ch. M. and Peppas, N. A., Adv. Polym. Sci. 151:37 (2000).

The term "hydrogel" as used herein refers to a hydrophilic cross-linked polymer capable of containing a large volume fraction of water. In some embodiments, hydrogels according to the disclosure can contain greater than about 70-90 volume % water. When a hydrophilic polymer is formed in situ, it may inherently acquire water from its environment or from solutions used to create the hydrogel.

Non-limiting representative examples of suitable hydrogels according to the disclosure are composed of a material selected from agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol) monomethacrylate, chitin, poly(hydroxyalkyl methacrylate), polyelectrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester cross-linked polyglucans, and derivatives and combinations thereof.

External molds can be used to shape the hydrogel component during polymerization. Additionally, by controlling the rate of polymerization, it may be possible to mold the biocompatible composite of the disclosure similar to how one would mold clay.

The mold provides the shape and support for the solidifying hydrogel composition. It is permeable, typically having pore-like cavities or interstices that are filled by the liquid-hydrogel composition. For example, the mold can be a porous polymer mesh, a natural or synthetic sponge, a piece of coral or hydroxyapatite having a desired porosity, or a matrix of metallic, inorganic, ceramic, or plastic struts. The permeability of the mold allows diffusion of nutrients outside the structure into the hydrogel-cell composition filling the mold (i.e., where the cells are) and the diffusion of waste products produced by the cells out of the structure through the hydrogel-cell composition, thereby promoting growth of the cells in the hydrogel-cell composition. Although other liquids, e.g., body fluids, may occupy the mold prior to being filled with the liquid hydrogel-cell composition, the hydrogel-cell composition will displace these liquids and rapidly harden within the mold.

The mold is shaped in the form of the tissue to be grown. For example, the mold can be shaped as a piece of cartilaginous tissue or bone tissue, such as a meniscus for a knee or elbow, a piece of bone to repair a bone defect, an ear, a nose, an internal organ, a ligament, a tendon, the trachea (as a conduit), mandibles, or skin. Depending on the material from which it is made, the mold can be shaped by cutting, molding, or casting, or any other method that produces the desired shape for the mold. The mold is also biocompatible (e.g., not toxic to the cells suspending in the hydrogel) and, in some cases, the mold can be biodegradable. The mold can be shaped either before or after the hydrogel (or hydrogel-cell) composition fills the mold. For example, a partially flexible support structure can be filled with the hydrogel composition and molded into a desired shape, e.g., by hand, as the hydrogel hardens.

Where cryogels are used, the cryogels are formed prior to addition of any cells. Furthermore, the cryogels can also be formed in a mold as described above with respect to hydrogels. Such porous materials can also be created through particle/salt leaching, foaming and the like.

The hydrogel-cell composition can be injected into the mold either before or after the support structure is implanted into a patient. As the hydrogel solidifies, it will adopt the flexibility and resiliency of the mold. Such resiliency and flexibility allows a mold that is saturated with hydrogel-cell composition to accommodate compressive and tensile forces.

The mold can be formed of a biocompatible, or biodegradable, synthetic polymer such as a polyanhydride, polyorthoester, or polyglycolic acid. The polymer should be chosen so that the resulting mold provides adequate shape and support for the cell-containing hydrogel suspension and allows nutrients to diffuse to the cells and promote cell growth and proliferation. Factors, including nutrients, growth factors, inducers of differentiation or dedifferentiation, products of secretions, immunomodulators, inhibitors of inflammation, regression factors, biologically active compounds which enhance or allow ingrowth of the lymphatic network or nerve fibers, and drugs, can be incorporated into the polymer support structure. An example of a suitable polymer is polyglactin, which is a 90:10 copolymer of glycolide and lactide.

Bone is a complex tissue with a composite extracellular matrix, consisting of an organic protein component (known as the osteoid) and an inorganic mineral phase, similar in structure to apatites such as hydroxyapatite ($Ca_5(PO_4)_3OH$) and dahllite (carbonated apatite). The osteoid on the other hand, consists predominantly of type I collagen along with other components frequently found in extracellular matrices and non-collagenous proteins such as osteocalcin, osteopontin, and bone sialoprotein. It is believed that the osteoid lends tensile strength while the mineral component provides rigidity to the tissue matrix. Mimicking this complex composite structure is essential for the development of synthetic bone graft materials that closely mimic natural bone. Such composite materials that mimic the structure of osseous and dental tissues also provide a tissue-specific microenvironment which can be harnessed to direct the differentiation of progenitor cells and stem cells into bone-specific cells. Mineralized polymeric materials thus have immense applications both as bone grafts and as scaffolds in bone tissue engineering. Hence, there has been a recent surge in efforts to study formation of composite materials consisting of calcium phosphate minerals and substrates derived from both, synthetic and natural polymers.

Although the exact mechanism responsible for the in vivo mineralization of osseous tissue is unclear, a well-demonstrated and prominent factor in this phenomenon is the protein-mediated nucleation of apatite. Bone sialoprotein (BSP) is a glutamate-rich protein believed to function as a nucleating agent in vivo through binding of calcium to the anionic glutamate residues. Similar studies have also illustrated the role of anionic residues of amelogenin in the mineralization of dental enamel matrix. Inspired by this mechanism, a popular method of inducing nucleation of calcium phosphate mineral phases is based on utilizing polymers with charged functional groups; thus initiating nucleation through binding of calcium or phosphate ions to anionic and cationic functional groups respectively.

The biomineralization process observed in nature during mineralization of bone tissue further emphasizes the potential role of matrix hydrophobicity on mineralization. For instance, despite being rich in anionic residues the aspartate-rich osteopontin (OPN) is less efficient at promoting mineralization than glutamate-rich bone sialoprotein (BSP) and under certain conditions does not nucleate apatites at all. The ability of peptides containing aspartate residues to suppress mineralization has also been demonstrated. One of the notable differences between the two proteins is that the glutamate residues (found in BSP) are more hydrophobic (longer alkyl chain) than aspartate resides (found in OPN). Thus, hydrophobicity of the templating matrix (independent of functionality) could be an important consideration in addition to functionality for biomineralization of synthetic matrices.

The disclosure is based, in part, on the evaluation of the effect of matrix hydrophobicity on nucleation of apatite-like phases on a polymeric substrate. This was accomplished by synthesizing hydrogels with varying hydrophobicity by utilizing N-acryloyl amino acids with different number of methylene ($CH_2$) groups of the pendant side chain terminating with a carboxyl group. These pendant side chains thus present $Ca^{2+}$ binding-carboxyl groups, which serve as nucleation sites for the formation of calcium phosphate minerals and modulate their crystallization. Additionally, varying the number of $CH_2$ groups in increments of two groups at a time systematically allows for subtle changes in the matrix hydrophobicity without changing the terminal functional group. The ability of these matrices to undergo templated mineralization was evaluated using multiple approaches involving both protein-dependent and $Ca^{2+}$-concentration dependent nucleation. The disclosure also provides methods and compositions wherein the porosity of a cryogel is controlled. Cryogels of the disclosure can comprise columnar oriented matrices or random "spongy" formed matrices. The porosity of the columnar and spongy formed cryogels provides designable artificial matrices having a desired porosity and nucleation density.

Accordingly, the disclosure provides a composition comprising a hydrophilic polymer suitable for forming a hydrogel or cryogel or macroporous scaffold and which comprises an acryloyl amino acid having identical or differing carbon chains terminating in a carboxyl group. In one embodiment, the hydrogel or cryogel comprises a homogenous-type of acryloyl amino acids. For example, in one embodiment, the hydrogel or cryogel comprises a single species of acryloyl amino acids such as $CH_2=CHCONH(CH_2)_nCOOH$, where n can be varied from 1 to 12 and any integer there between. In another embodiment, the hydrogel or cryogel or macroporous scaffold comprise a species of acryloyl amino acids of $CH_2=CHCONH(CH_2)_2COOH$. In another embodiment, the hydrogel or cryogel or macroporous scaffold comprise a species of acryloyl amino acids of $CH_2=CHCONH(CH_2)_3COOH$. In another embodiment, the hydrogel or cryogel or macroporous scaffold comprise a species of acryloyl amino acids of $CH_2=CHCONH(CH_2)_4COOH$. In another embodiment, the hydrogel or cryogel or macroporous scaffold comprise a species of acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof. The carboxyl group is capable of reacting with $Ca^{2+}$ and subsequently nucleating a calcium phosphate mineral. In a further embodiment, the hydrogel- or cryogel-acryloyl amino acid composition leads to the formation of apatite, thereby mimicking bone tissue.

The disclosure also provides cryogels having a lamellar columnar structure with a pore size of approximately 50-60 µm in the dried state (corresponding to ~100-150 µm in the swollen state) and comprising an acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof. In another embodiment, the disclosure provides a macroporous network consisting of more randomly oriented, interconnected cellular pores measuring approximately 20-30 µm in diameter in the dried state (corresponding to 50-60 µm in the swollen state) and comprising an acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof.

In some embodiments, the hydrogel or cryogel or macroporous scaffolds described above are mineralized with calcium and/or phosphate. In another embodiment, the hydrogel or cryogel or macroporous scaffold comprise proteinaceous material from serum. In yet another embodiment, the hydrogel or cryogel or macroporous scaffold comprise proteinaceous material from serum and are mineralized. In yet further embodiments, any of the foregoing cryogels or hydrogels or macroporous scaffold are seeded with cells in vitro or in vivo.

As described more fully herein, the disclosure provides biocompatible composites including a polymeric hydrogel or cryogel or macroporous scaffold comprising a surface moiety comprising a carbon chain of from about 2-8 carbons in length (e.g., 2, 3, 4, 5, 6, 7 or 8) terminating in a carboxyl group for use in repairing defects in tissue and the preparation of tissue compositions for bone regenerating or other tissue regeneration (e.g., cartilage). In some embodiments, the surface moiety comprises an acryloyl amino acid. In another embodiment, the hydrogel or cryogel composition comprises a plurality of acryloyl amino acids of different lengths. The biocompatible composite may be formed in vivo, which allows for repair of any shaped defect, does not require the formation of a distinct repair site, and allows for minimally invasive surgery. In some embodiments, the biocompatible composite may be used to repair bone. In such a case, the biocompatible composite may be formed within a bone to be repaired or may be formed ex vivo and then inserted, contacted or otherwise placed at the site in need of repair. In one embodiment, the hydrogel or cryogel is seeded with autologous cells (parenchymal or stem cells alone or in combination with fibroblasts, osteoclasts, chondrocytes and the like).

The biocompatible composites (e.g., the hydrogels or cryogels or macroporous scaffold) of the disclosure can be introduced as a bulking agent for hard tissue defects, such as bone or cartilage defects or osteochondral, either congenital or acquired disease states, or secondary to trauma. The composites can be introduced either with or without seeded cells. It will be recognized that the composites may be seeded with a desirable cell type prior to implantation or following implantation. Furthermore, the hydrogels and cryogels or macroporous scaffold can serve as a scaffold for cellular infiltration once placed in vivo.

The biocompatible composition can be seeded with cells (e.g., allogenic, autologous, stem cells including mesenchymal stem cells, embryonic stem cells, induced stem cells) prior to polymerization or after polymerization of a hydrogel, or following formation of the macroporous structure or cryogel. In yet a further embodiment, the biocompatible composition can be formed and then combined with an artificial or natural serum preparation to expose the composition to calcium and phosphate to promote apatite formation. In yet another embodiment, the composite can then be seeded with cells (e.g., bone cells, stem cells or the like).

The seeded composite can then be cultured in vivo for a sufficient time to allow cells to grow into or on the composite or may be implanted into a subject, whereby the cells grow on or in the composite.

As mentioned above, the hydrogels or cryogels of the disclosure may contain mammalian cells, such as, e.g., human cells, in order to promote tissue repair. Non-limiting representative examples of suitable cells that may be incorporated into the hydrogel or subsequent to cryogelation include fibroblasts, chondrocytes, osteoblasts, osteoblast-like cells, stem cells, and combinations thereof. Preferably the cells are from a compatible human donor. More preferably, the cells are from the patient (i.e., autologous cells). The cells may be incorporated into a portion or the entirety of one or more phases (or one or more layers of a phase) of the hydrogel or cryogel of the disclosure. Moreover, one or more cell types may be distributed throughout a hydrogel or cryogel or macroporous scaffold.

Stromal cells include, for example, chondrocytes chondrocyte-progenitors, fibroblasts or fibroblast-like cells, with or without other stromal cells, and can be inoculated onto or into the hydrogel of cryogel of the disclosure. Growth factors may be added prior to, during or subsequent to inoculation of the stromal cells to promote proliferation, infiltration and/or growth. Alternatively, the cells may be genetically engineered to express and produce a desired factor or therapeutic agent; such cells can include genetically engineered stromal cells. These cells would serve as a source of therapeutic protein or other protein factor(s).

As used herein, "chondrocyte" shall mean a differentiated cell responsible for secretion of extracellular matrix of cartilage. Preferably the cells are from a compatible human donor. Preferably, the cells are from the patient (i.e., autologous cells) or are derived from a stem cell source.

As used herein, "fibroblast" shall mean a cell of connective tissue that secretes proteins and molecular collagen including fibrillar procollagen, fibronectin and collagenase, from which an extracellular fibrillar matrix of connective tissue may be formed. Fibroblasts synthesize and maintain the extracellular matrix of many tissues, including but not limited to connective tissue. The fibroblast cell may be mesodermally derived, and secrete proteins and molecular collagen including fibrillar procollagen, fibronectin and collagenase, from which an extracellular fibrillar matrix of connective tissue may be formed. A "fibroblast-like cell" means a cell that shares certain characteristics with a fibroblast (such as expression of certain proteins).

Stromal cells such as chondrocytes may be derived from articular cartilage, costal cartilage, etc. which can be obtained by biopsy (where appropriate) or upon autopsy. Fibroblasts can be obtained in quantity rather conveniently from foreskin or, alternatively, any appropriate cadaver organ. Fetal cells, including fibroblast-like cells, chondrocyte-progenitors, or other stem cells (omnipotent or pluripotent) may be obtained from umbilical cord or placenta tissue or umbilical cord blood, fetal tissue, or through induced pluripotent stem cells. Such stem cells can be used to prepare a "generic" stromal or cartilaginous tissue.

The disclosure provides a comprehensive and systematic study on mineralization of calcium phosphates on hydrogels as well as porosity of macroporous structures (e.g., such as those of cryogels) with varying pendant side chain lengths (e.g., varying hydrophobicity), presenting terminal carboxyl functional groups. Binding of $Ca^{2+}$ to the functional groups of the matrix leads to the initial nucleation of mineral phases and is the first step in the templated mineralization of the anionic substrate. It is thus conceivable that any changes that alter the accessibility of terminal carboxyl group for $Ca^{2+}$ binding could potentially change the matrix assisted templated mineralization process.

Distinct differences in mineralization were observed depending on the mineralization methods used. The hydrogels that exhibited relatively little mineralization in simulated body fluid showed rapid, extensive mineralization upon immersion in serum-supplemented simulated body fluid (approximately 72 hours in serum-supplemented simulated body fluid, as compared to approximately 3 weeks in serum-free simulated body fluid). This is especially interesting, as the $Ca^{2+}$ and $HPO_4^{2-}$ concentrations were similar in both solutions. Mineralization in serum supplemented simulated body fluid is likely to be mediated through proteins that are adsorbed on biocompatible composite surfaces. It is important to note that albumin, fibronectin and laminin have been previously reported to play a role in the nucleation of hydroxyapatite. Apparently, certain proteins can have a dual role on the mineralization of apatites, functioning as either a nucleator or inhibitor depending on their conformation and accessibility; these proteins that act as nucleators when adsorbed on a substrate while acting as inhibitors of substrate mineralization when in solution.

In order to explain the difference observed in mineralization in the metastable $Ca^{2+}/HPO_4^{2}$ solution in absence of proteins, it is necessary to consider the effect of pendant side chain length on both $Ca^{2+}$ binding and nucleation capacity. For example, increases in matrix hydrophobicity tend to promote co-operative $Ca^{2+}$ binding to carboxyl residues. It is also possible that hydroxyapatite/CaP mineral formation was favored by longer side chains (or optimal side chain lengths) that support the accessibility of the terminal carboxyl groups at the surface. The increased flexibility in longer side chains could allow the $Ca^{2+}$ bound chains to attain a conformation favoring the formation of apatite crystals through similarity to their nucleated faces. Such conformational mimicking of nucleation faces by ion-binding sites has been implicated as a possible mechanism influencing biomineralization observed in nature. The chain length-dependent difference in accessibility could also be a causative factor leading to variation in the morphology of the crystals when the hydrogels were immersed in 40 mM $Ca^{2+}$/24 mM $HPO_4^{2-}$. The disclosure demonstrates, for example, that A6ACA hydrogels have the optimal side chain length to promote templated mineralization under all the immersion procedures utilized.

A consideration is the accessibility of the carboxyl group to ions in the hydrogel-cation interface (aqueous), as this accessibility affects $Ca^{2+}$binding. A6ACA was found to optimally bind to divalent transition metal cations. It is possible that A6ACA hydrogels have an optimal balance between the length of the hydrophobic side chain and the hydrophilic character of the terminal carboxyl group. Solubility calculations involving these hydrogels have suggested that pendant side chains containing more than six groups tend to collapse inward due to increases in side chain hydrophobicity, thereby severely reducing accessibility of the terminal carboxyl groups. Thus, the reduced accessibility due to inward collapse of the pendant side chain from A8ACA adequately explains the observed drop in mineralization. It is interesting to note the presence of hydroxyapatite peaks in the XRD spectra for A8ACA hydrogels immersed in serum supplemented SBF despite the lack of observed surface calcification. This could be due to limited nucleation of apatite on the collapsed side chains in the hydrogel interior mediated by the imbibed metal solutions. This is further supported by the sheet-like morphology of the mineralized phase on A8ACA hydrogels immersed in 40 mM $Ca^{2+}$/24 mM $HPO_4^{2-}$ suggesting a lack of nucleation sites on the surface.

The disclosure demonstrates that small changes in matrix interfacial hydrophobicity (the ability of the matrix to interact with surrounding aqueous milieu) independent of functionality can profoundly influence the $Ca^{2+}$binding and formation of hydroxyapatite-like mineral phases on hydrogel matrices. While increasing pendant side chain length promotes mineralization for chains containing about five methylene groups, further increase in side chain length can lead to inward collapse of the pendant side chain and subsequently result in a reduction of apatite nucleation ability. Pendant side chain length can thus affect the extent of mineralization as well as the topology of the mineralized phase. These findings show a synergistic effect between functionality and the accessibility of that functionality on the mineralization of polymeric materials, and provide a plausible rationale for the differences in apatite-nucleating ability of osteopontin and bone sialoprotein. The developed approaches can be used to develop mineral-polymer composite materials for use as scaffolds in bone tissue engineering and as bone grafts as well as in other applications requiring the templated synthesis of organic/inorganic composite materials.

Furthermore, the disclosure demonstrates that pore formation can be controlled in cryogels. Such porosity is useful for nucleation and cellular infiltration. The disclosure demonstrates that ability to control pore architecture in macroporous cryogels during cryogelation by controlling the directionality of the cooling front, obtaining cryogels with a lamellar, columnar pore structure as well as spongy pore architecture. Further, the disclosure demonstrates that in macroporous cryogel scaffolds, cellular, isotropic pore architecture promotes early osteogenic differentiation of human mesenchymal stem cells to a greater extent than lamellar, oriented pore structure. In vivo, the presence of a mineral phase in these cryogels promoted ectopic bone formation irrespective of pore architecture, although pore microarchitecture did significantly influence host cell infiltration and vascularization in the absence of a mineral phase.

The following examples are intended to illustrate but not limit the disclosure. While they are typical of those that might be used, other procedures known to those skilled in the art may alternatively be used.

EXAMPLES

Example 1

N-acryloyl 2-glycine (A2AGA), N-acryloyl 4-aminobutyeric acid (A4ABA), N-acryloyl 6-aminocaproic acid (A6ACA) and N-acryloyl 8-aminocaprylic acid (A8ACA) were synthesized from glycine (Fisher Scientific Inc), 4-aminobutyeric acid, 6-aminocaproic acid and 8-aminocaprylic acid (Acros Organics Inc) respectively.

Poly (ethylene glycol)-diacrylate (MW: 6000 Da) (PEGDA-6K) was used as a crosslinker and was synthesized from poly (ethylene glycol) (MW: 6000 Da) (Fluka Analytical Inc).

Simulated body fluid (m-SBF) was prepared as specified by Oyane et al. Briefly, 1 L of a HEPES-NaOH buffered solution (pH 7.4) in ultrapure water was prepared, containing 142 mM $Na^+$, 5 mM $K^+$, 1.5 mM $Mg^{2+}$, 2.5 mM $Ca^{2+}$, 103 mM $Cl^-$, 10 mM $HCO_3^-$, 1.0 mM $HPO_4^{2-}$ and 0.5 mM $SO_4^{2-}$. This was sterilized and filtered using a 0.22 μm sterilizing, low protein binding vacuum filter system (Corning Inc). The solution was stored at 4° C. and warmed to 37° C. prior to usage. Where serum preparations were used, 400 ml of SBF were combined with 100 ml fetal bovine serum (Premium Select, Atlanta Biologicals). This mixture was sterilized and filtered using a 0.22 μm sterilizing, low protein binding vacuum filter system (Corning Inc). The solution was stored at 4° C. and warmed to 37° C. prior to usage. All immersions were conducted under sterile conditions.

2.74 g of dipotassium phosphate trihydrate ($K_2HPO_4.3H_2O$) (Acros Organics) and 2.22 g $CaCl_2$ (Acros Organics) were added to 500 ml ultrapure water. 6N HCl was then added dropwise until the disappearance of the resultant turbidity. Prior to usage, 1 M Tris-HCl (pH 7.5) was added dropwise to gradually adjust the pH to 5.2, the highest pH at which precipitation was not observed for the duration of the immersion.

Example 1

Hydrogels

Synthesis of Hydrogels. 0.001 moles of each of the monomers (0.1291 g, 0.157 g, 0.185 g and 0.213 g for A2AGA, A4ABA, A6ACA and A8ACA, respectively) was dissolved in 1 ml 1M NaOH to ensure complete deprotonation, thereby obtaining 1 M solution of the sodium salt of each of the monomers. 0.05 g of PEGDA 6K was added as a cross-linker to the solution of each monomer, yielding a final solution containing 5% PEGDA 6K (w/v). The precursor solutions were subjected to redox polymerization using 0.5% ammonium persulfate as initiator and 0.1% N,N,N',N'-tetramethylethylene diamine (TEMED) as accelerator. This precursor solution was poured into glass moulds and allowed to proceed for 15 minutes at room temperature. The resultant hydrogels measured approximately 0.1 cm in thickness, 8.2 cm in length and 1.5 cm in height. Un-reacted components were leached out of the hydrogels by immersion in DI water for 48 hours with changing the water intermittently. These hydrogels were then sterilized by immersion in 70% ethanol for 24 hours and air-dried under sterile conditions.

In their semi-dried state, hydrogels were confined between two glass slides, and allowed to dry further. This was done in order to prevent curving of the hydrogels during the drying process. The water contact angles of the hydrogels were determined by a sessile drop method at 20° C. using goniometer (CAM100, KSV Instruments Ltd.). A 5 µL droplet of water was placed on the surface of hydrogels, following which the droplets were imaged and the angles were calculated using CAM100 software. All samples were prepared as triplicates and results were shown as a mean value with standard deviation.

Mineralization of Hydrogels. Dried hydrogels were swollen in simulated body fluid. Upon equilibration, hydrogels were cut into circular samples and used for mineralization.

Following mineralization, the hydrogels were thoroughly rinsed with running DI water. They were then flash-frozen with liquid $N_2$ and lyophilized for characterization.

Mineralization of hydrogels by immersion in protein-supplemented simulated body fluid. The hydrogels (n=3 for each monomer) were immersed in serum-supplemented simulated body fluid for a period of two weeks, with daily exchange of solution to ensure continuous supply of ions.

Mineralization of hydrogels by immersion in 40 Mm $Ca^{2+}$/24 mM $HPO_4^{2-}$ solution.

Hydrogels (n=3 for each monomer) were immersed in 40 mM $Ca^{2+}$/24 mM $HPO_4^{2-}$ for 30 minutes and then rinsed with DI water. These were then immersed in simulated body fluid for 24 hours—this entire process was considered as one immersion cycle. Hydrogels were mineralized through one and two such immersion cycles respectively.

Adsorption of serum proteins on hydrogel surfaces. The hydrogels (n=3 for each monomer) were immersed in fetal bovine serum (Premium Select, Atlanta Biologicals) for 4 hours at 37° C. They were then transferred to a fresh vessel and washed with Laemmli sample buffer—this was to ensure that proteins eluted on the sample buffer were proteins adsorbed on the gels and not the surface on which immersion with FBS was carried out. Solutions collected from replicates for each monomer were pooled and subjected to electrophoresis with SDS-PAGE. Proteins were visualized through staining with Coomassie Brilliant Blue G-250 of the polyacrylamide gels following electrophoresis.

Lyophilized hydrogels were sputter coated with Cr (Denton Desk IV Sputter Coater) and imaged using Phillips XL30 ESEM to study microstructural topology and composition of hydrogel-mineral composites was studied using Oxford EDX attachment and INCA analysis software.

Lyophilized mineral-hydrogel composites were powdered and analyzed by powder X-ray diffraction using a Rigaku RU200Bh DMax-RB rotating anode diffractometer. The X-ray source was a Cu anode generating Cu $K_{\alpha1}$ x-rays ($\lambda$=0.154056 nm). The diffractometer was operated at 40 kV beam energy and 120 mA beam current. A graphite monochromater [0002] orientation (2d=0.6708 nm) was used and the diffracted beam was collected into a horizontal goniometer covering an angular range (2θ) from 5° to 80°. The collected spectra were analyzed using MDI Jade X-Ray analysis software employing PDF-4+ ICDD database for search match peak identification.

For gels mineralized through immersion in serum-supplemented SBF, each lyophilized gel (n=3 for each monomer) was homogenized in 0.5 ml 0.5 N HCl; for gels mineralized through immersion in 40 mM $Ca^{2+}$/24 mM $HPO_4^{2-}$, each lyophilized gel was homogenized in 1 ml 0.5N HCL.

This homogenate was vigorously vortexed for 24 hours at 4° C. in order to completely dissolve the calcium phosphate mineral. The $Ca^{2+}$ concentration in this solution was measured by spectrophotometric analysis with cresolphthalein complexone, using Calcium Reagent (two part liquid) set (Pointe Scientific Inc) and used to determine the $Ca^{2+}$ content in the original lyophilized sample. The calculated $Ca^{2+}$ content was normalized to the dry weight of the sample.

For immersion in serum-supplemented simulated body fluid, statistical analysis was carried out using one way ANOVA; for immersion in 40 mM $Ca^{2+}$/24 mM $HPO_4^{2-}$, two-way ANOVA was used. Microsoft Excel 2007 was used for statistical analysis.

Scanning Electron Microscopy. Mineralized and non-mineralized hydrogels soaked in PBS were flash frozen using liquid nitrogen and lyophilized. Samples were sputter-coated with Cr (Sputter coater) and analyzed using Philips XL30 ESEM to study microstructural topology. Elemental analysis was carried out using Oxford Energy Dispersive Spectra (EDS) attachment and analyzed using Inca software package.

Sterilization of substrates for cell culture. Mineralized and non-mineralized hydrogels, as well as plasma-treated tissue culture glass coverslips (Fisherbrand) were sterilized by immersion in 70% ethanol for 6 hours, and then immersed in excess of sterile PBS for 4 days with twice daily exchange of PBS to remove residual ethanol. Samples were then immersed in growth medium consisting of high glucose DMEM (GIBCO), 8.97% fetal bovine serum (Hyclone, Atlanta Biologicals), 0.9% L-glutamine (GIBCO) and 50 units/ml penicillin/streptomycin (GIBCO) for 16 hours at 37° C. prior to cell seeding. Samples can also be sterilized by other methods known in the art (e.g., ethylene oxide sterilization).

Cell seeding and imaging. hMSCs (p7071L, Tulane University) were expanded in growth medium (see above for composition) and passaged at 60-70% confluence. At passage 6 (P6), these cells were seeded on the various substrates at 5,000 cells/cm$^2$ and cultured in growth medium at 37° C., 5% $CO_2$ for up to 21 days. Cells were visualized with bright-field microscopy (Carl Zeiss Axio Observer A1). Images of cells on mineralized hydrogels were subjected to contrast enhancement using ImageJ (National Institutes of Health, Bethesda, Md.) to improve cell visibility due to opacity of these hydrogels. Cell shape was quantified via shape index (SI), using measurements from ImageJ, detailed below:

$$SI = \frac{4\pi A}{p^2} \quad (1)$$

Where SI is the shape index, A is the cell area and p is the perimeter.

Proliferation analysis. Samples (n=3 per group, per time point) were collected at 1, 7, 14 and 21 days and frozen at −80° C., following which they were lyophilized. Samples were then digested with 1 ml of papain solution (125 µg/ml papain [Worthington Biochemical Corporation], 10 mM L-cysteine [Sigma], 100 mM phosphate and 10 mM EDTA, pH 6.3) for 16 hours at 60° C. DNA was measured using Quant-IT Picogreen dsDNA Kit (Invitrogen).

Immunofluorescent staining. At 14 and 21 days, samples were fixed in 4% paraformaldehyde (pH 7.4) and immediately stained for osteocalcin. Briefly, fixed samples were blocked/permeabalized in PBS containing 3% bovine serum albumin, 0.1% Triton-X for 30 minutes. Samples were then incubated with primary antibody (Mouse monoclonal to osteocalcin, [ab13420, Abcam]) diluted 1:100 in blocking solution for 1 hour at room temperature. After washing with PBS for 15 minutes, samples were incubated with secondary antibody and phalloidin, diluted 1:250 and 1:100 in blocking solution. Samples were then mounted with Vectashield-DAPI (Vector Laboratories) and imaged using a Zeiss Observer A1 microscope equipped with an X-Cite 120 (EXFO) mercury lamp.

Quantitative RT-PCR. Total RNA was extracted from samples (n=4 per group per time point) at 0, 4, 7, 14 and 21 days using TRIzol (Invitrogen) according to the manufacturer's protocol and reverse transcribed to cDNA using iScript cDNA synthesis kit (Bio-Rad). Real-time quantitative PCR reactions were performed using SYBR Green PCR Master-mix on an ABI Prism 7700 Sequence Detection System (Perkin Elmer/Applied Biosystems). Target gene expression was normalized using glyceraldehydes 3-phosphate dehydrogenase (GAPDH) as housekeeper. The level of expression of each target gene was calculated as previously reported. Primer sequences are provided in Table 3.

TABLE 3

| Gene | Gene (Abbreviation) | Direction | Primer Sequence (SEQ ID) |
|---|---|---|---|
| Glyceraldehyde 3-phosphatase | GAPDH | Forward | 5' CAT CAA GAA GGT GGT GAA GC 3' (1) |
| | | Reverse | 5' GTT GTC ATA CCA GGA AAT GAG C 3' (2) |
| Osteocalcin | OCN | Forward | 5' GAA GCC CAG CGG TGC A 3' (3) |
| | | Reverse | 5' CAC TAC CTC GCT GCC CTC C 3' (4) |
| Runt-related Transcription Factor 2 | RUNX2 | Forward | 5' CCA CCC GGC CGA ACT GGT CC 3' (5) |
| | | Reverse | 5' CCT CGT CCG CTC CGG CCC ACA 3' (6) |
| Bone Sialoprotein | BSP | Forward | 5' AAT GAA AAC GAA GAA AGC GAA G 3' (7) |
| | | Reverse | 5' ATC ATA GCC ATC GTA GCC TTG T 3' (8) |
| Osterix | OSX | Forward | 5' CAT CTG CCT GGC TCC TTG 3' (9) |
| | | Reverse | 5' CAG GGG ACT GGA GCC ATA 3' (10) |

Dissolution studies. Acellular mineralized and non-mineralized hydrogels were incubated in 1.5 ml growth medium at 37° C. and 5% $CO_2$. Twice a week, half of the medium was removed and replaced with fresh medium to mimic cell culture conditions. Samples (n=3 per group per time point) were collected at 0, 7, 14 and 21 days. Samples were then analyzed for calcium content as previously described ([37]) Briefly, samples were frozen at −80° C. and lyophilized for 24 hours. The dry weights of the lyophilized samples were measured, after which samples were homogenized and vigorously vortexed in 0.5 M HCl for 16 hours at 4° C. Calcium content was measured using o-cresolphthalein complexone by Two Reagent Kit (Pointe Scientific).

In a separate experiment, mineralized samples (n=3 per immersion solution) were immersed in both, 1.5 ml hMSC growth medium and 50 mM Tris (pH 7.4) respectively at 37° C. 200 μl of each immersion solution was collected from the samples every 24 hours and replaced with 200 μl fresh solution for upto 1 week. Calcium concentration in the collected solutions was measured using two reagent set (Pointe Scientific); phosphate concentration was measured using molybdenum yellow.

Effect of soluble $Ca^{2+}$ and $PO_4^{3-}$ concentration on hMSC differentiation. P6 hMSCs were seeded on tissue culture polystyrene (TCPS) surfaces and cultured in three types of media: (a) control growth medium ([$Ca^{2+}$]: 1.9 mM, [$PO_4^{3-}$]: 1 mM) (b) high-calcium growth medium ([$Ca^{2+}$]: 3 mM, [$PO_4^{3-}$]: 1 mM) supplemented with $CaCl_2$ and (c) high-phosphate growth medium ([$Ca^{2+}$]: 1.9 mM, [$PO_4^{3-}$]: 5 mM) supplemented with $Na_2HPO_4$ and $NaH_2PO_4$. Samples were collected using TRIzol for gene expression analysis as detailed above at 3 days and 7 days of culture.

Example 2

Cryogels

Cryogel synthesis. Cryogels were prepared in cylindrical polypropylene molds measuring 3 mm in diameter. For columnar cryogels, 40 μl of DI $H_2O$ was added to the molds and chilled at −20° C. prior to cryogelation to create a thin ice layer at the bottom of the mold (referred to as 'columnar molds'). For cryogels with spongy pore structure, molds were chilled at −20° C. without DI $H_2O$ (referred to as 'spongy' molds). Both spongy and columnar molds were chilled in a covered dry polystyrene petri dish.

A solution of 9.25% w/v A6ACA, 20% w/v PEGDA 3.4K was prepared in 0.5M sodium hydroxide and chilled to 4° C. for 1 hour. To this chilled precursor solution, 0.15% tetramethylethylenediamine and 0.5% ammonium persulfate were added to initiate polymerization. Immediately, 60 μl of the resulting solution was added to spongy and columnar molds respectively, placed inside covered dry polystyrene petri dishes. This setup was then placed at −20° C. and allowed to polymerize for 24 hours. Following polymerization, both spongy and columnar cryogels were removed from molds, thawed at room temperature and immersed in 1× phosphate-buffered saline (PBS) for 24 hours (with 2× change of solution) to remove the unreacted materials.

Cryogel sterilization. Cryogels were then sterilized by immersion in 70% ethanol for 12 hours and washed in 1× sterile PBS for at least 3 days (with at least 2× daily change of solution) to remove residual ethanol.

Micro-computed tomography. The cryogels were soaked in a 10% solution of $FeCl_3$ in DI $H_2O$ for 2 hours, frozen at −80° C., and then lyophilized. The function of the $FeCl_3$ was to provide $Fe^{3+}$ ions to bind to the anionic A6ACA moieties, causing iron salt formation on the internal surface of the cryogels upon lyophilization. This $FeCl_3$ salts on the internal pore layer served to increase contrast during radiographic imaging. 3-dimensional internal pore structure of the cryogels was non-invasively imaged using SkyScan 1076 High Resolution In-Vivo Micro-Computed Tomography Scanner (Skycan, Belgium), at 9 μm/pixel resolution. Scans were reconstructed from projections using NRecon software (Sky- Scan, Belgium) and converted to 3-dimensional objects using DataViewer software (Skyscan, Belgium). Additionally, porosity measurements were carried out via CTAn software (Skyscan, Belgium).

Scanning Electron Microscopy. The microstructures of PEGDA-co-A6ACA cryogels were examined using a scanning electron microscopy (SEM, Philips XL30 ESEM). Briefly, the samples were dehydrated in 50%, 75%, and 100% ethanol and dried using a critical point dryer (Tousimis AutoSamdri 815). After samples were completely dried, they were Iridium-coated using a sputter coater (Emitech K575X Sputter Coater) for 8 seconds prior to SEM imaging.

Porosity. Mercury intrusion porosimeter (MIP) (Micromeritics AutoPore IV9500, Oak Ridge, Tenn., USA) was used to determine the internal pore size distribution, pore-surface area, and porosity. Briefly, the samples were serially dehydrated in 50%, 75%, and 100% ethanol. They were then dried using a critical point dryer (Tousimis AutoSamdri 815) in which they were subjected to a pressure cycle starting at approximately 0.5 psia, increasing to 60000 psia. Based on the amount of intrusion of mercury into samples via their internal pore structures, the analysis was performed using an AutoPore IV9500 v1.07 software. A total of 0.1 g of each sample was used for the measurement.

Cell culture. Human mesenchymal stem cells (Center for Regenerative Medicine, Texas A & M University) were expanded at 37° C., 5% $CO_2$ in growth medium consisting of high-glucose DMEM (Gibco), 8.97% fetal bovine serum (Hyclone), 1.8 mM L-glutamine (Gibco), and passaged at 70% confluence using 0.25% trypsin-EDTA (Invitrogen). Cells were utilized at passage 6 for seeding within the cryogel scaffolds. Cryogels were immersed in growth medium at 37° C., 5% $CO_2$ for 18 hours prior to cell seeding.

Cell seeding. At time of seeding, cryogels were dried under sterile conditions for 105 minutes, resulting in an approximately 50% and 40% loss of weight through evaporation for spongy and columnar cryogels, respectively. Cryogels were then seeded at a density of $8 \times 10^5$ cells/construct. Briefly, hMSCs were suspended in growth medium at $1.33 \times 10^7$ cells/ml. 60 µl of this suspension was then seeded on top of each construct at various spots. The seeded constructs were then incubated in the absence of medium at 37° C., 5% $CO_2$ for 3 hours to allow for cell attachment. Following this, cell-laden cryogels were incubated in growth medium for 24 hours at 37° C., 5% $CO_2$. Subsequently, cryogels were cultured for up to 21 days in osteogenic medium consisting of high-glucose DMEM (Gibco), 10% FBS (Hyclone), 10 mM β-glycerolphosphate (Calbiochem), 100 nM dexamethasone (Sigma), 10 µg/ml ascorbic acid-2-phosphate (Sigma), and 50 units/ml penicillin-streptomycin (Gibco). Medium was changed every 48 hours and samples were collected for analysis as detailed below.

Quantitative PCR. Cell-laden cryogels (constructs) were analyzed for expression of osteogenic markers as a function of culture time at 0, 4, 7, 14, and 21 days. Constructs (n=3 per group, per time point) were homogenized in TRIzol (Invitrogen); RNA was extracted from this homogenate according to the manufacturer's instructions. 800 ng of RNA was reverse-transcribed to cDNA using iScript cDNA synthesis kit (Bio-Rad) according to the manufacturer's instructions. The resultant cDNA was then analyzed for expression of osteogenic markers—Runx2, osteocalcin (OCN), and osteopontin (OP) with glyceraldehyde 3-phosphate dehydrogenase (GAPDH) as a housekeeping gene. Expression at each time point was normalized to day 0 and expressed as fold change thereof. Real-time PCR reactions were run on a Model 7300 Real-time PCR Cycler (Applied Biosystems), using Power SYBR I Mastermix (Applied Biosystems). Expression level of various genes was calculated.

Alkaline phosphatase activity. Spongy and columnar cryogels were assayed for activity of alkaline phosphatase (ALP) using enzymatic dephosphorylation of para-nitrophenol-phosphate (p-NPP) to para-nitrophenol (n-NP) at various time points (4, 7, 14 and 21 days) via ALP Substrate Kit (Bio-Rad). Briefly, constructs (n=3 per group per time point) were homogenized in 500 µl of 0.75 M of 2-amino-2-methyl-1-propanol (pH 10.3) on ice and stored at −20° C. Assay substrate solution was prepared according to the manufacturer's instructions. 120 µl of sample solution was combined with 480 µl of assay substrate solution and incubated at room temperature for 2 minutes; the absorbance of this solution was measured at 405 nm every 30 seconds for 7 minutes using a DU730 UV/Vis spectrophotometer (Beckman Coulter). A graph of absorbance vs. time was plotted and the slope was determined via a linear fit to calculate the rate of reaction. A higher slope indicates increased ALP activity. ALP activity was expressed as change in absorbance per minute per construct wet weight.

Calcium content. Constructs were assayed for calcium content at 7 and 21 days. At each time point, cell-seeded as well as acellular cryogels (n=3 per group) were collected and lyophilized. After measuring their dry weight, lyophilized constructs were homogenized in 0.5 ml of 0.5 M HCl. The homogenates were vigorously vortexed for 16 hours at 4° C. The calcium concentration was measured spectrophotometrically at 570 nm via o-cresolphthalein complexone using a two reagent calcium kit (Pointe Scientific) according to the manufacturer's instructions. The total calcium content of each construct was normalized to its dry weight. Moreover, poly(ethylene glycol) hydrogels-containing A6ACA moieties have been previously shown to undergo mineralization in serum-supplemented solutions containing $Ca^{2+}$ and $PO_4^{3-}$ (Phadke et al., 2010). To correct for this, the Ca content of the corresponding acellular construct was subtracted from the average cellular Ca content of the cell-seeded constructs.

Mineralization of cryogels. Mineralized samples were prepared by a procedure described previously with some modifications (Phadke et al., 2010). Cryogels were immersed in DI $H_2O$ for 24 hours, dried at 37° C. and swollen in simulated body fluid (SBF) as detailed above. The SBF-swollen cryogels were then partially dried for 60 minutes at room temperature on tissue paper to remove excess SBF from the pores and immersed in a solution of 40 mM $Ca^{2+}$/24 mM $HPO_4^{2-}$ at pH 5.2 for 1 hour on an orbital shaker at 300 rpm at 25° C. Following immersion, cryogels were rinsed briefly in running DI $H_2O$ and incubated in SBF for 48 hours, with daily change of solution. The samples were then soaked in PBS for 6 hours, sterilized by immersion in 70% ethanol for 6 hours and incubated in sterile PBS for 3 days with at least 2× daily solution change to remove residual ethanol.

Cell seeding of mineralized cryogels. For cellular mineralized constructs, mineralized cryogels were incubated in hMSC growth medium for 18 hours, dried under sterile conditions for 105 minutes and seeded with hMSCs at passage 6 as detailed above. Cell-seeded cryogels were incubated in growth medium at 37° C., 5% $CO_2$ for 1 week prior to subcutaneous implantation.

General Methodology for Hydrogels and Cryogels

Subcutaneously implanted samples were explanted following animal sacrifice and photographed to assess host cell infiltration. Samples were then fixed in 4% PFA in PBS for 96 hours and stored in 70% ethanol at 4° C.

Histology for in vitro samples. Constructs cultured in vitro were collected at 21 days of culture for histology. Samples were fixed for 24 hours in 4% paraformaldehyde (PFA) and stored in 70% ethanol at 4° C. The fixed constructs were dehydrated in graded concentrations of ethanol followed by subsequent immersion in Histo-Clear (National Diagnostics), embedded in paraffin and cut into 10 µm thick sections.

Sections were then analyzed through immunofluorescent staining for osteocalcin. Briefly, the sections were deparaffinized in xylene and gradually rehydrated through a series of decreasing ethanol concentrations. The re-hydrated sections were blocked with blocking buffer consisting of 3% bovine serum albumin (Sigma), 0.1% Triton-X 100 (Sigma) in PBS for 30 minutes and then exposed to primary antibody (osteocalcin anti-mouse, monoclonal) (Abcam, ab13420) diluted 1:100 in blocking buffer for 1 hour. After washing sections with PBS (30 minutes), samples were exposed to secondary antibody (Alexa Fluor 568 goat anti-mouse) diluted 1:250 in blocking buffer for 60 minutes. Following this, sections were washed with PBS for 30 minutes, mounted on glass slides with Vecta Shield/DAPI (Vector Laboratories) and visualized via fluorescent microscopy.

Micro-computed tomography of subcutaneously implanted samples. Samples were visualized through micro-computed tomography simultaneously during fixation in PFA with SkyScan 1076 High Resolution In-Vivo Micro-Computed Tomography Scanner (SkyScan, Belgium), at 9 µm/pixel resolution. Scans were reconstructed from projections using NRecon software (SkyScan, Belgium) and converted to 3-dimensional models using CTAn software (SkyScan, Belgium).

Histology of subcutaneously implanted samples. Samples were embedded in paraffin, sectioned and stained via hematoxylin-eosin (H & E). For immunohistochemical staining, unstained sections were deparaffanized in xylene and gradually rehydrated through series of decreasing ethanol concentrations. Sections were then blocked with blocking buffer for 60 minutes at room temperature, following which they were exposed to primary antibody (osteocalcin anti-mouse, Abcam, ab14320) diluted 1:100 in blocking buffer for 18 hours at 4° C. Sections were then washed in PBS for 30 minutes and exposed to 0.3% hydrogen peroxide in PBS for 20 minutes at room temperature to block endogenous peroxidase activity. Samples were exposed to HRP-conjugated secondary antibody (goat anti-mouse IgG-HRP, Santa Cruz Biotechnology, sc-2031) for 60 minutes at room temperature, washed with PBS for 30 minutes and developed using diaminobenzidine (DAB) substrate kit (ThermoFisher) according to the manufacturer's instructions. Samples were then briefly washed with PBS to remove excess DAB and visualized using bright-microscopy.

Analysis

N-acryloyl amino acid hydrogels with varying hydrophobicity were synthesized using PEGDA (MW: 6 kDa) as a crosslinker (see FIGS. 1A-E for chemical structure and nomenclature of the hydrogels). The effect of pendant side chain length on hydrophobicity (e.g., greater pendant side chain length increases matrix hydrophobicity) was confirmed through contact angle measurements (See FIGS. 1F-G). The hydrogels were mineralized through three methods: (a) immersion in simulated body fluid, (b) immersion in simulated body fluid supplemented with fetal bovine serum, and (c) immersion in a metastable solution of 40 mM $Ca^2$/24 mM $HPO_4^{2-}$. Scheme 1A is a representation of the process of nucleation of calcium phosphate mineralized phases through $Ca^{2+}$ binding to anionic surface moieties while Scheme 1B represents mineralization through physisorption of proteins.

Scheme 1: Schematic representation for mineralization of polyanionic hydrogels (here for A2AGA) under (A) Protein-free conditions and (B) In the presence of serum proteins. Shown are $PO_4^{3-}$ ions; $Ca^{2+}$ ions; Hydrogel interior; serum proteins.

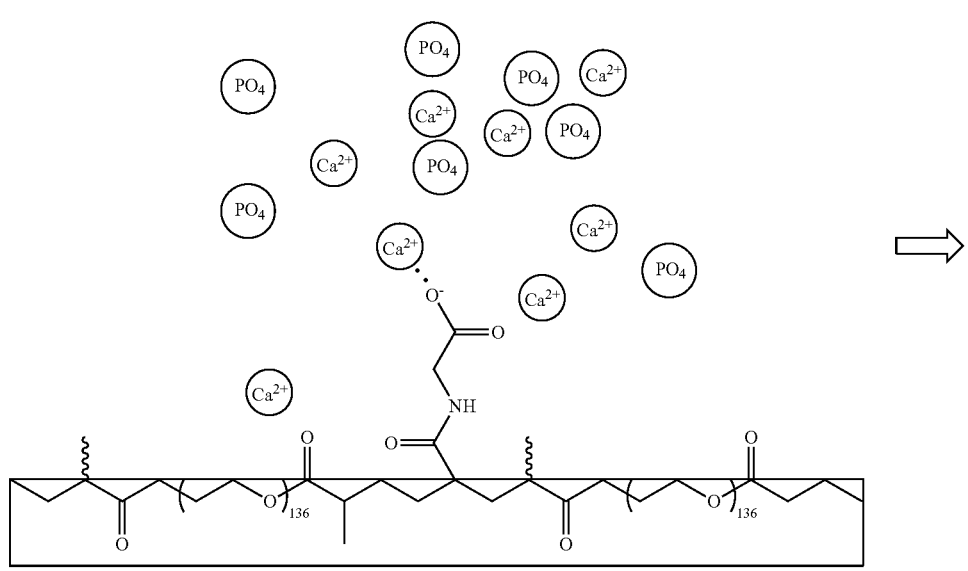

A

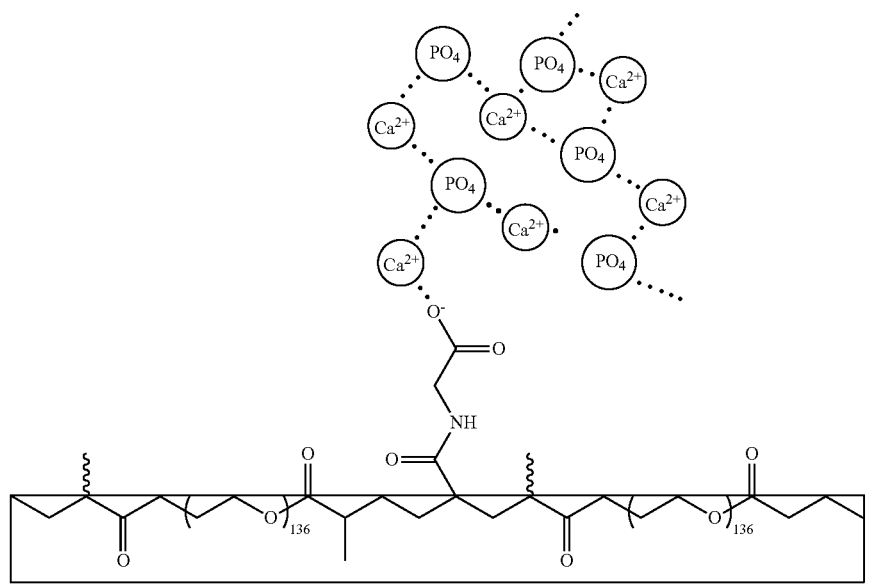
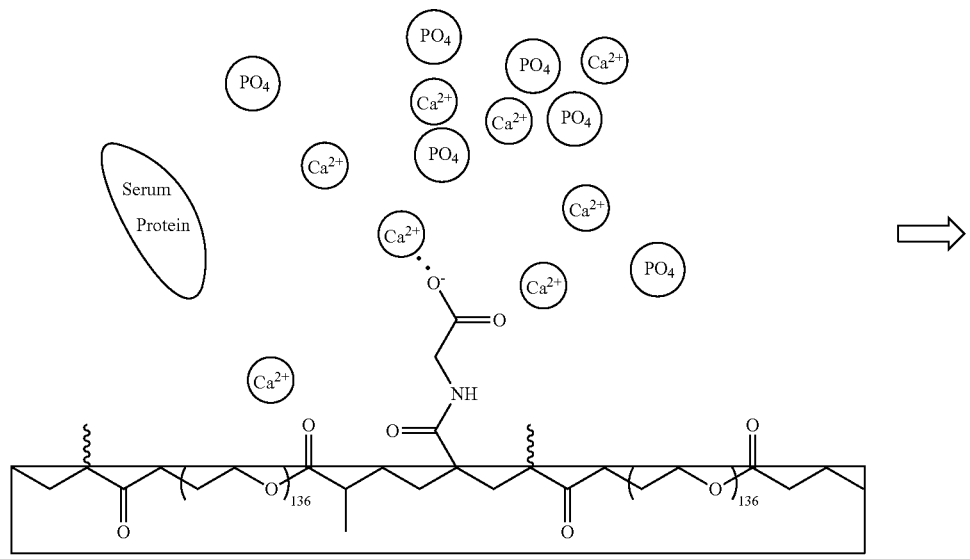

-continued

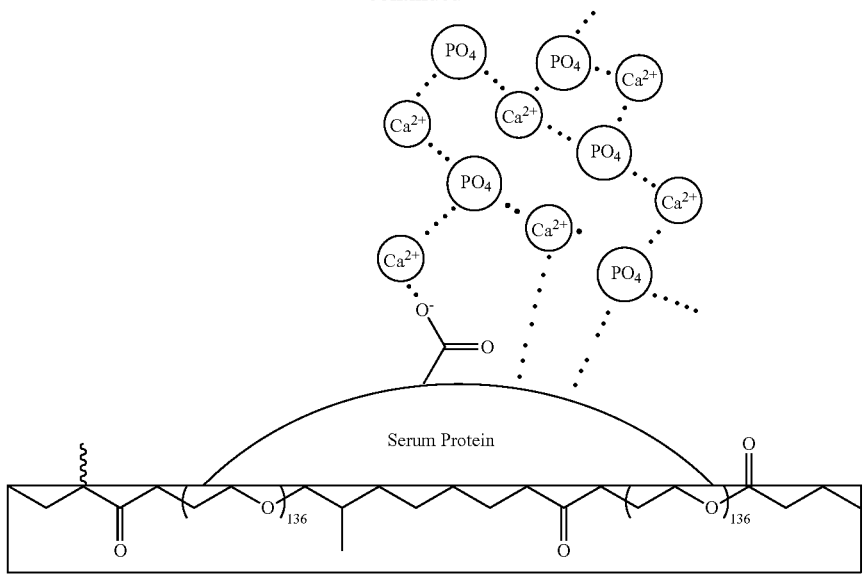

Figure 6:
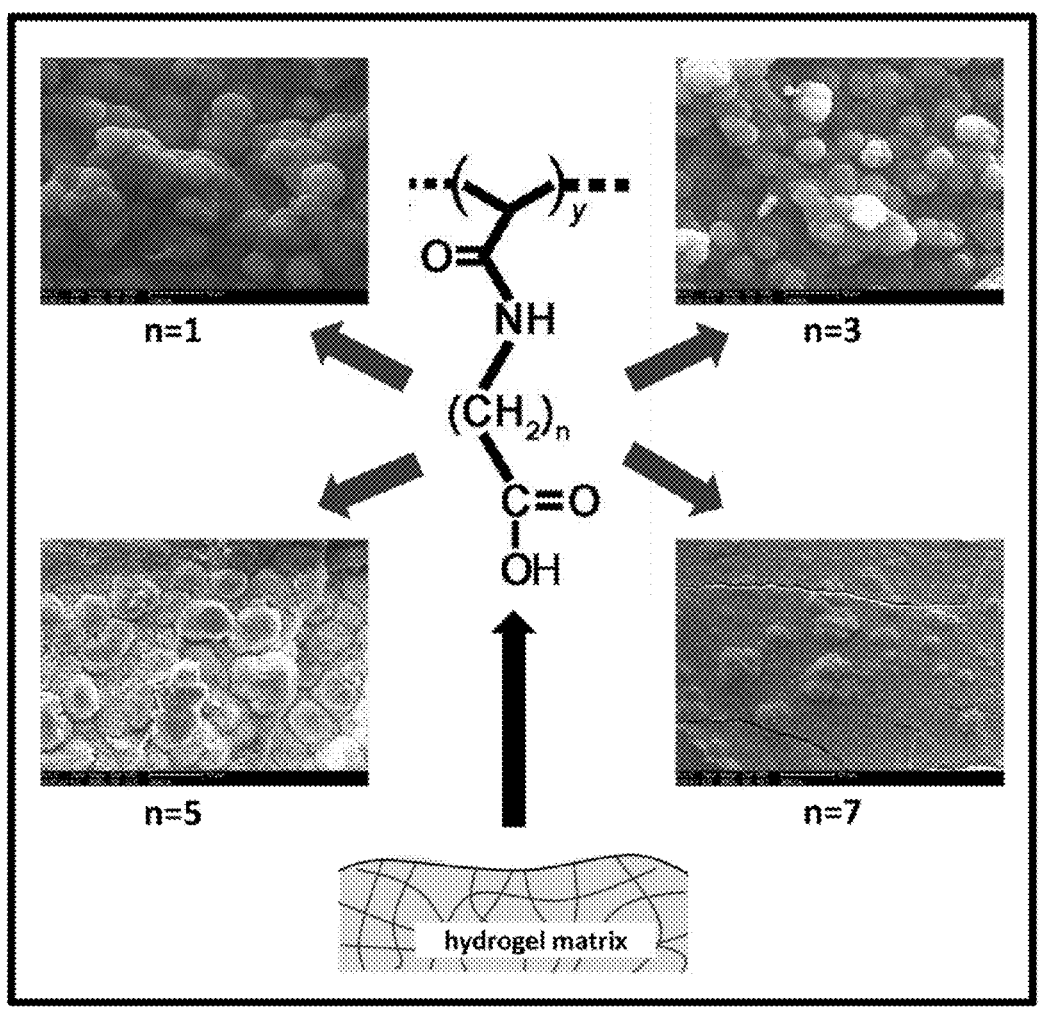
FIG. 6 depicts micrographs of compositions of the disclosure with different chain lengths.

Simulated body fluid was chosen for immersion because it closely mimics the ionic concentrations and pH typically observed in plasma. Upon soaking in simulated body fluid, faint white mineral deposits on A6ACA hydrogels were observed after approximately three weeks of immersion. While an analysis of $Ca^{2+}$ content of these hydrogels using the calcium assay was not sufficiently sensitive to detect a difference in calcium content of the various hydrogels, analysis with scanning electron microscopy (SEM) showed the formation of spherical particles consisting mainly of calcium phosphate for A6ACA hydrogels (see FIG. 6); deposits seen in other hydrogels (A2AGA, A4ABA, A8ACA) were found to be devoid of phosphate, as evidenced by the elemental analysis by Energy Dispersion Spectra (EDS).

Figure 7:
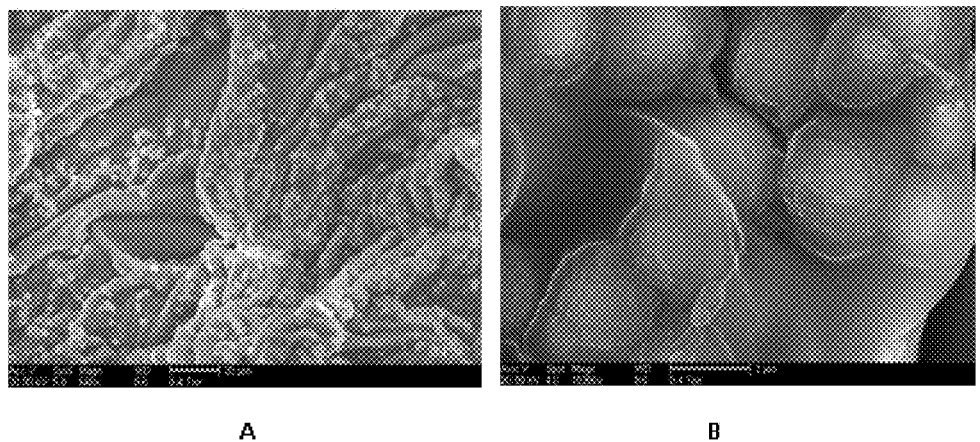
FIGS. 7A-B shows scanning Electron Microscopy images at (A) low magnification and (B) high magnification of Ca/P particles deposited on A6ACA/PEGDA 6K mineralized by immersion in simulated body fluid for 3 weeks.
Figure 8:
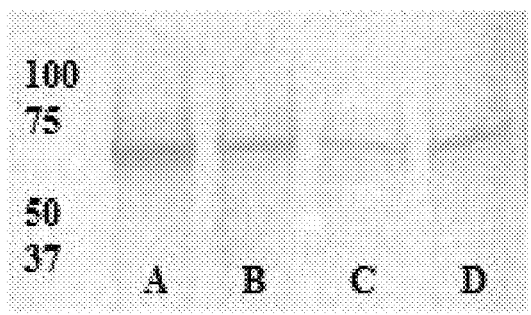
FIG. 8 is a gel with Coomassie blue staining showing adsorption of serum proteins on (Lane A) A2AGA, (Lane B) A4ABA, (Lane C) A6ACA and (Lane D) A8ACA.
Figure 9:
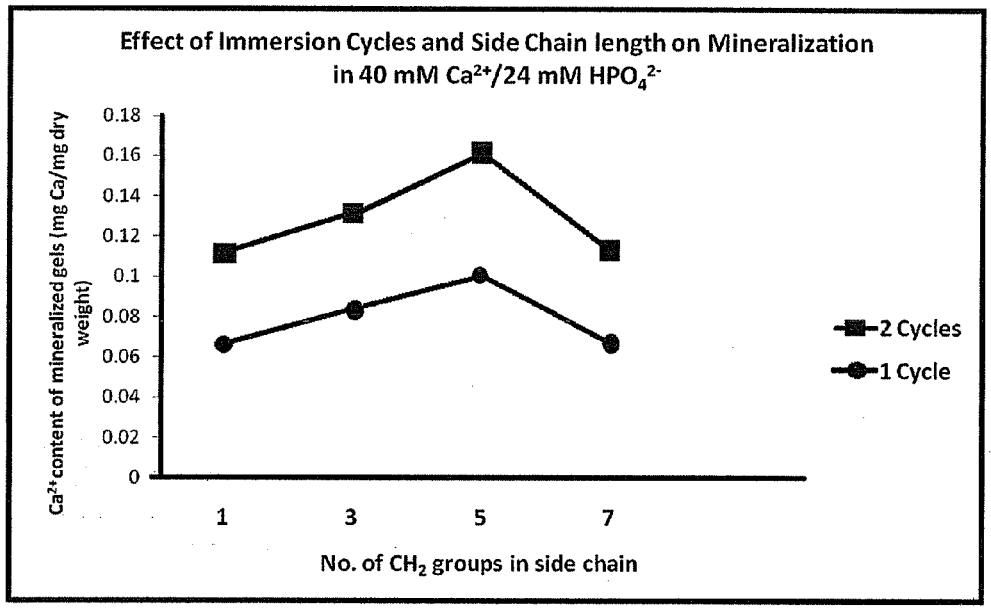
FIG. 9 is a graphical representation of effect of immersion cycles and side chain length on templated mineralization of hydrogels.

The simulated body fluid was supplemented with fetal bovine serum and evaluated for the ability of serum proteins to promote mineralization. The ability of serum proteins such as fibronectin and albumin to nucleate apatite-like minerals under physiological conditions as well as the affinity for proteins such as albumin to charged polymeric substrates has been well established. Under these circumstances, the mineralization was faster than in the case of protein-free simulated body fluid, first appearing after 72 hours of immersion and peaking within 1 week of immersion despite an identical concentration of $Ca^{2+}$ and $HPO_4^{2-}$ in both solutions. Additionally, a pronounced and significant trend (One way ANOVA; P<0.001) was observed wherein an increase in mineralization was observed concomitant an increase in side chain length as illustrated by increase in $Ca^{2+}$ content, peaking for A6ACA, followed by a decrease for A8ACA (FIG. 2A). These differences in rate and extent of mineralization suggest that adsorption of proteins from the serum onto the hydrogel surfaces played a role in the nucleation of minerals as per the mechanism in Scheme 1B (see also FIGS. 7A-B). The adsorption of proteins on the respective gels was confirmed through elution, followed by visualization by Coommassie blue staining (FIG. 8).

Figure 3:
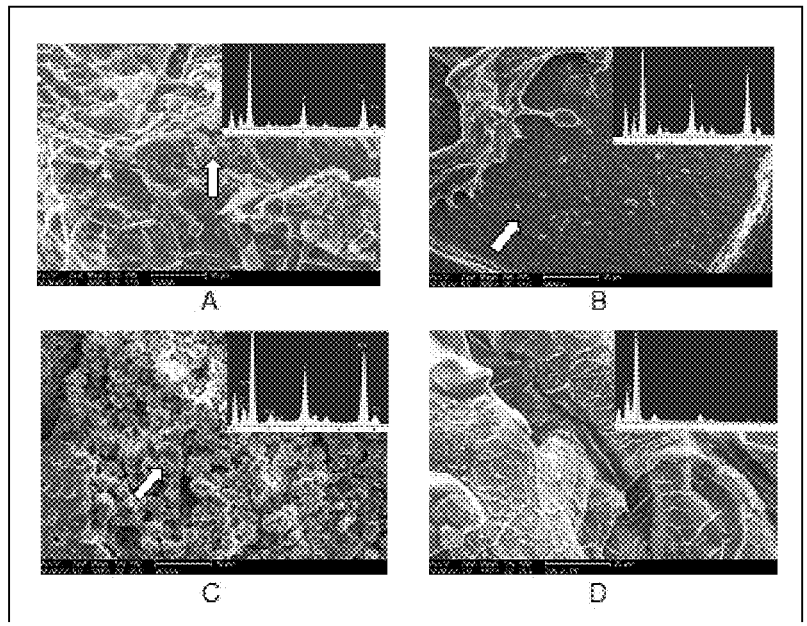
FIGS. 3A-D show scanning Electron Microscopy images and Energy Dispersion Spectra (inset) of hydrogels containing (A) A2AGA (B) A4ABA (C) A6ACA (D) A8ACA, mineralized by immersion in serum supplemented SBF. Note that (D) shows the absence of any observable deposits containing calcium phosphate as seen in the EDS. Arrows indicate the calcium phosphate particles.

Upon microscopic examination with SEM-EDS, A2AGA, A4ABA, A6ACA hydrogel surfaces exhibited continuous layers of calcium phosphate particles with calcium/phosphate ratios of approximately 1.7, 1.7 and 1.6 respectively, as evidenced by elemental analysis through EDS; A8ACA hydrogels did not show any calcium phosphate deposits and showed minimal $Ca^{2+}$ content (FIG. 3). The similarity of the Ca/P ratios of the mineral phases on the hydrogels to that of synthetic hydroxyapatite (1.67), suggests the formation of an apatite-like phase. This was confirmed through XRD analyses (FIG. 2B), which indicated peaks corresponding to the diffraction spacing observed in hydroxyapatite (PDF-4-010-6312, based on PDF4+ ICDD database). This suggests the formation of semicrystalline hydroxyapatite on the hydrogels under physiological conditions. Other peaks observed include those corresponding to halite (NaCl) as well as unidentified peaks, presumably due to ordering within the gel due to the PEGDA oligomer (6 kDa), which is used as a crosslinker for the hydrogels (See table 1 for detailed information on hydroxyapatite peaks observed in the XRD spectra of the hydrogels).

TABLE 1

Detailed information relating to peaks corresponding to hydroxyapatite identified in the X-ray diffractive spectra for hydrogels with varying hydrophobicity, mineralized by immersion in serum-supplemented simulated body fluid.

| Monomer used | Number of Methylene Groups in Side Chain | Hydroxyapatite peaks identified | | Relative Intensity | |
|---|---|---|---|---|---|
| | | $2\theta$ | d(Å) Phase | Peak Height/ Background | % H (Relative to most intense peak) |
| A2AGA | 1 | 25.943 | 3.4420 | 540 | 52.2 |
| | | 31.739 | 2.8265 | 1162 | 100 |
| A4ABA | 3 | 31.659 | 2.8265 | 945 | 100 |
| A6ACA | 5 | 25.778 | 3.4420 | 150 | 39.2 |
| | | 31.682 | 2.8265 | 311 | 81.2 |
| A8ACA | 7 | 38.040 | 2.3676 | 711 | 42.3 |
| | | 62.840 | 1.4807 | 122 | 7.2 |
| | | 66.160 | 1.4133 | 154 | 9.2 |

The effect of matrix hydrophobicity on templated mineralization independent of protein-surface interactions as per the mechanism outlined in Scheme 1A was also examined. Since the $Ca^{2+}$ and $HPO_4^{2-}$ concentrations in simulated body fluid were too low (2.5 mM for $Ca^{2+}$ and 1.0 mM for $HPO_4^{2-}$)

to promote extensive formation of a mineralized phase independent of proteins (as observed in experiments involving immersion in simulated body fluid), a method was developed utilizing a metastable solution containing elevated concentrations of $Ca^{2+}$ (40 mM) and $HPO_4^{2-}$ (24 mM). This method takes advantage of the high solubility of calcium phosphates under acidic conditions. However, employing a low pH solution will result in protonation of the carboxyl functional groups on the hydrogels, thereby reducing the number of available $Ca^{2+}$-binding sites. By slowly raising the pH of this acidic solution through dropwise addition of 1 M Tris HCl (pH 7.5), the pH of the solution was raised to 5.2 while maintaining stability of the solution (without any observed turbidity for the duration of the 30 minute immersion). Significantly, this value was well above the $pK_1$ values (pertaining to the protonation/deprotonation of the terminal carboxyl group) of all the monomers, believed to be similar to those of the parent amino acids (See Table 2). This ensured that the protonation of the carboxyl groups did not compete with the binding of the pendant side chains to $Ca^{2+}$.

TABLE 2

Monomers used to vary matrix hydrophobicity.

| Monomer | No. of Methylene groups in side chain | Parent Amino Acid | $pK_1^{Ref}$ |
|---|---|---|---|
| A2AGA | 1 | Glycine | 2.34 |
| A4ABA | 3 | 4-Aminobutyeric Acid | 4.23 |
| A6ACA | 5 | 6-Aminocaproic Acid | 4.37 |
| A8ACA | 7 | 8-Aminocaprylic Acid | 4.62 |

$pK_1$ indicates the pK of the carboxyl group in the parent amino acid.

Figure 4A:
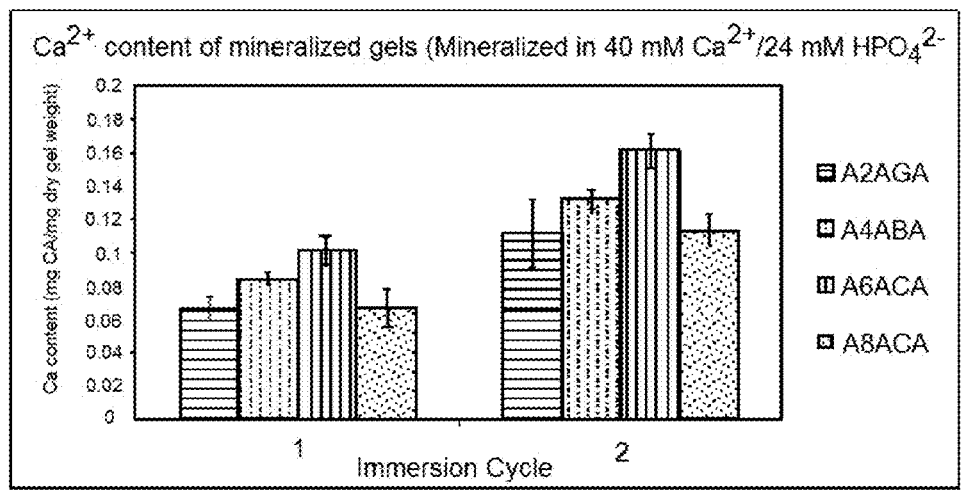
FIGS. 4A-B shows (A) Degree of mineralization (measured as the total $Ca^{2+}$ content in the mineralized hydrogels, normalized to dry gel weight) for hydrogels containing amino acid monomers with varying pendant side chain length, mineralized by immersion in 40 mM $Ca^{2+}$/24 mM $HPO_4^{2-}$. Error bars represent standard deviation. (B) X-ray diffraction spectra for hydrogels containing amino acid monomers with (B1) A2AGA (B2) A4ABA (B3) A6ACA and (B4) A8ACA respectively mineralized by immersion in 40 mM $Ca^{2+}$/24 mM $HPO_4^{2-}$", with a control sample of each hydrogel (non-mineralized) containing the respective amino acid monomer for comparison. Arrows indicate hydroxyapatite peaks (PDF-04-010-6312 in PDF-4+ database).
Figure 4B:
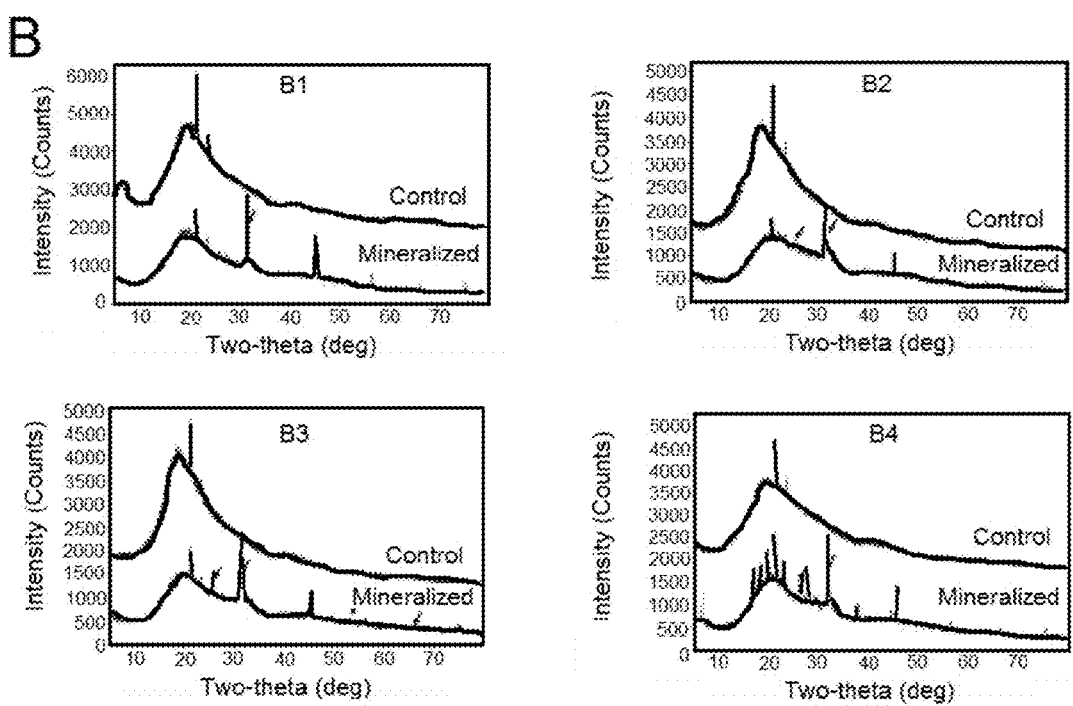
Figure 5:
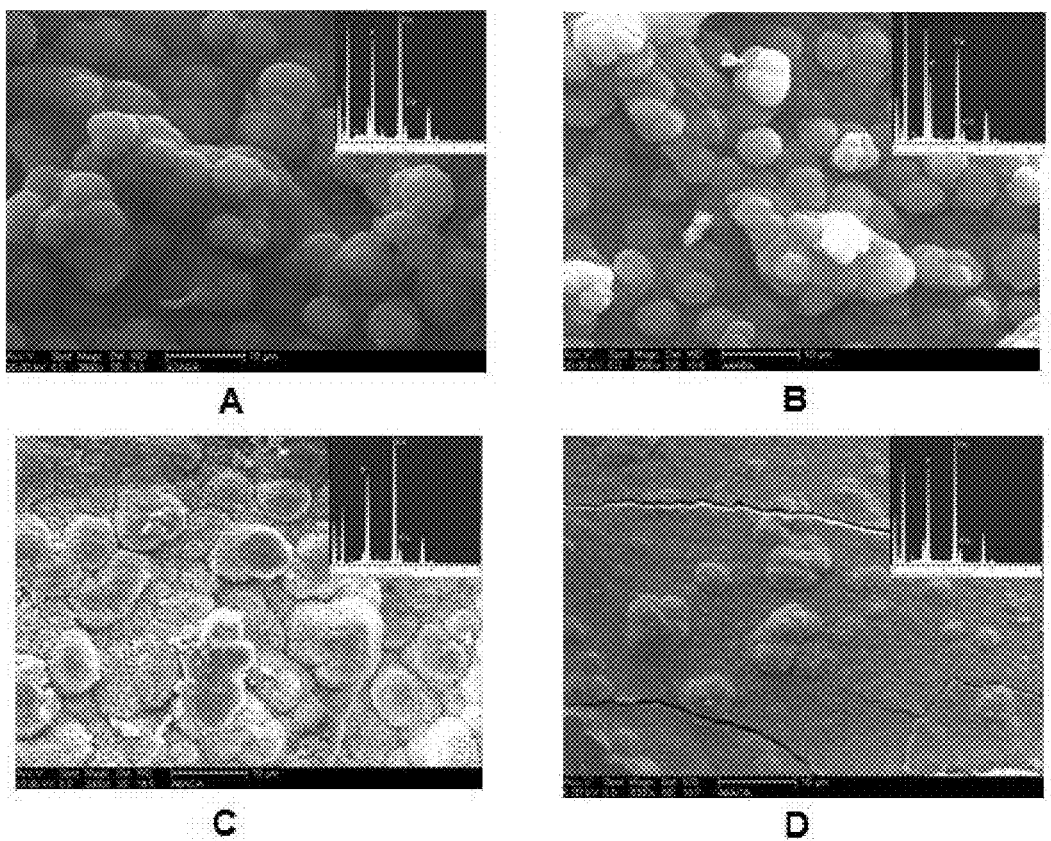
FIGS. 5A-D shows scanning Electron Microscopy images and Energy Dispersion Spectra (inset) of hydrogels containing (A) A2AGA (B) A4ABA (C) A6ACA (D) A8ACA, mineralized by immersion in 40 $Ca^{2+}$/24 mM $HPO_4^{2-}$.

White mineral deposits were observed on hydrogels irrespective of their pendant side chain length within the first 30 minutes of immersion in the metastable solution. As observed with serum-supplemented SBF, calcium content increased with pendant side chain length with A6ACA hydrogels showing the maximum calcium content, which then decreased for A8ACA. Moreover, there was an increase in $Ca^{2+}$ content for all hydrogels irrespective of chain length for two immersion cycles as compared to the hydrogels undergoing only 1 immersion cycle (FIG. 4A). (Two-way ANOVA ($\alpha$=0.05); side chain length, P<0.001; number of cycles, P<0.001; interaction of variables, P=0.56). SEM micrographs of the hydrogels revealed the formation of spherical calcium phosphate particles; it was observed that the mineralized phases in A2ACA, A4ABA, A6ACA and A8ACA showed a difference in morphology (FIG. 5). A2ACA and A4ABA both showed the formation of well defined smooth spherical particles; A6ACA showed clusters of many highly porous particles of similar diameter and A8ACA showed scattered, irregularly shaped particles on a sheet-like calcium phosphate layer. The Ca/P ratio as determined by EDS analysis, was found to be 1.4, 1.4, 1.6 and 1.6 for mineralized hydrogels synthesized with A2ACA, A4ABA, A6ACA and A8ACA respectively, suggesting again the formation of an apatite-like mineral. XRD analyses revealed that while analysis of phases formed on all hydrogels yielded multiple peaks corresponding to hydroxyapatite (PDF-4-010-6312, based on PDF4+ ICDD database), mineralized phases formed on hydrogels containing A6 and A8 respectively showed greater similarity to hydroxyapatite (FIG. 4B). As in the hydrogels mineralized by immersion in serum/FBS, diffraction peaks those corresponding to halite (NaCl) as well as unidentified peaks, presumably due to ordering within the polymeric hydrogels arising from the PEG chains, were also observed. These results support the observation from mineralization studies in serum-supplemented simulated body fluid, wherein longer chain length is more conducive to facilitate the formation of apatite like phases.

Figure 10:
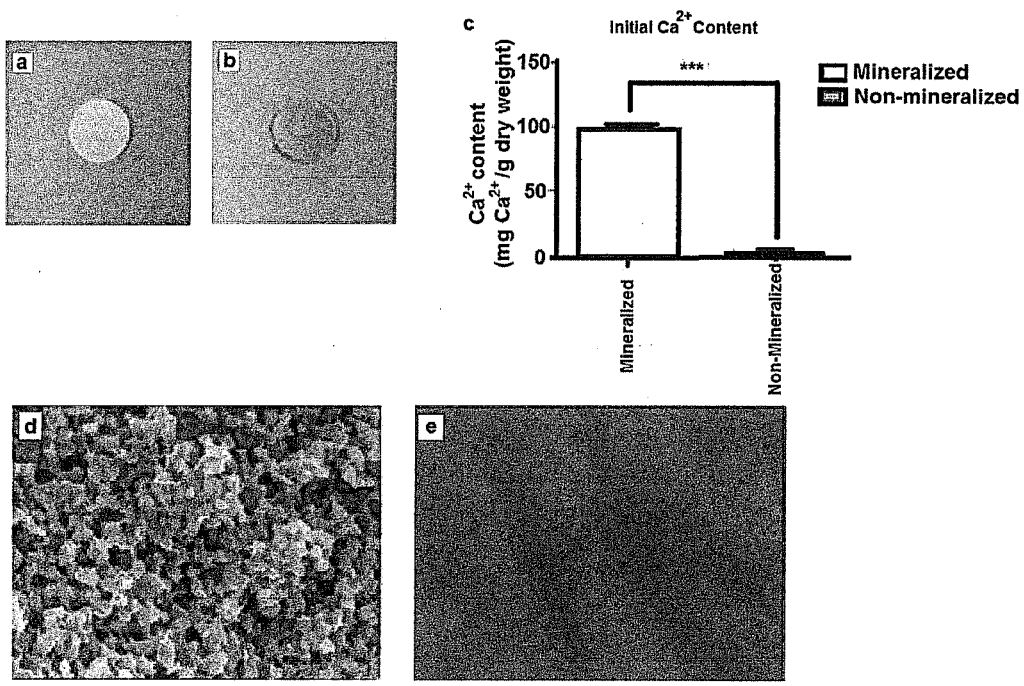
FIGS. 10A-E provides a characterization of hydrogels. Photographs of (A) mineralized and (B) non-mineralized hydrogels. (C) Initial $Ca^{2+}$ content of the mineralized and non-mineralized hydrogels prior to cell culture; asterisks indicate statistical significance (two-tailed, unpaired t-test, ***: p<0.001) (D,E) Scanning electron microscopy images of (D) mineralized and (E) unmineralized hydrogels.

Material characterization. A6ACA hydrogels were mineralized through immersion in calcium phosphate-containing solution; $Ca^{2+}$ binding to the terminal carboxyl groups of A6ACA promoted the subsequent nucleation of an inorganic calcium phosphate phase. Mineralized hydrogels appeared white in color, in comparison to non-mineralized hydrogels which were transparent in appearance (FIGS. 10A-B). Measurement of calcium concentration confirmed the calcification of mineralized samples, which contained 98±2 mg $Ca^{2+}$/g dry weight, as compared to non-mineralized hydrogels which contained 2±1 mg $Ca^{2+}$/g dry weight (FIG. 10C). Scanning electron microscopy of mineralized hydrogels showed a layer of irregularly shaped spherulites roughly 0.5 µm in diameter (FIG. 10D), but was not observed in non-mineralized samples (FIG. 10E). Elemental analysis showed that these minerals consisted chiefly of calcium phosphate with a Ca/P ratio of approximately 1.5; this is close to the Ca/P ratio observed in other bioactive ceramics such as $\beta$-tricalcium phosphate (1.5) and hydroxyapatite (1.67), suggesting the presence of an apatite-like mineral phase.

Figure 11:
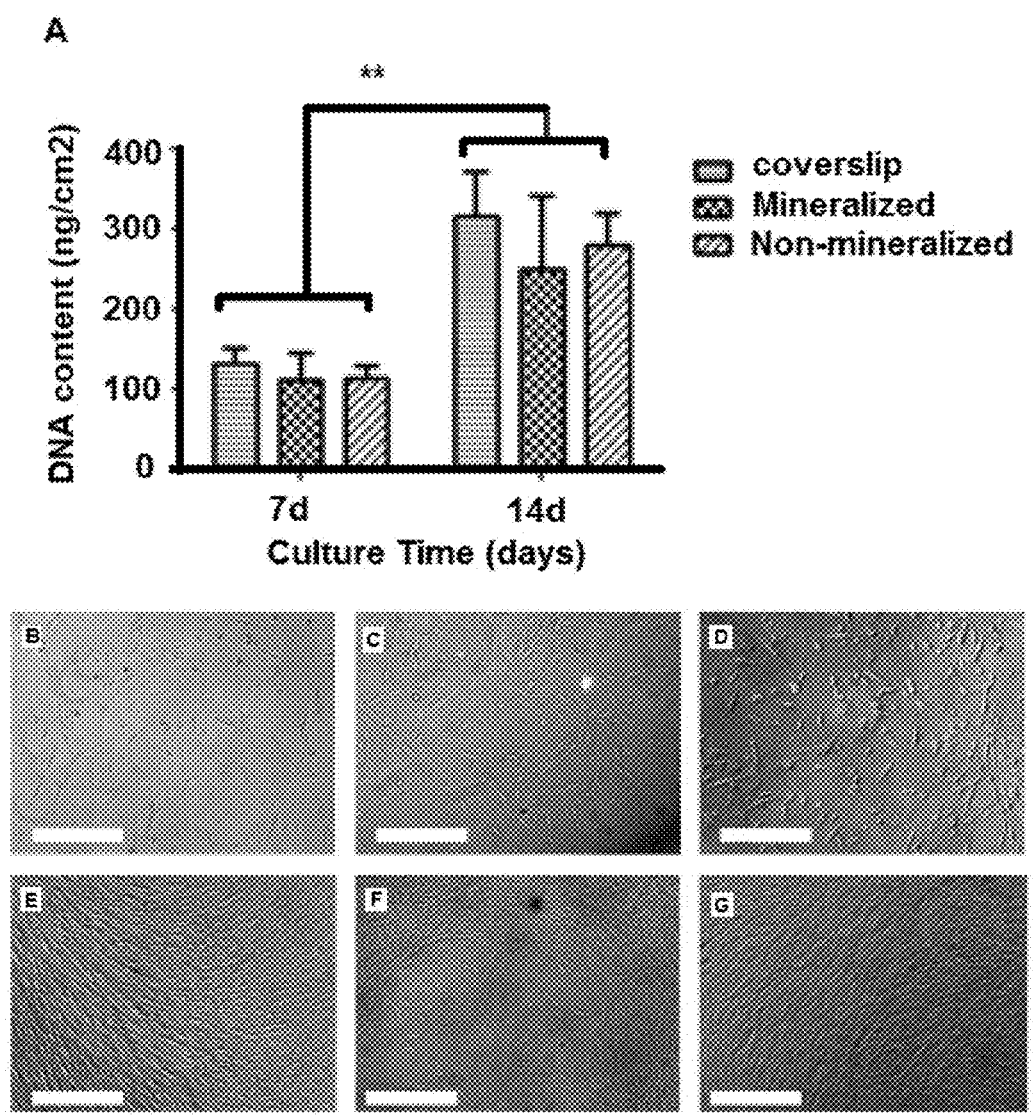
FIGS. 11A-G shows cell number and morphology on hydrogels. (A) DNA content (representing cell number) on coverslips, mineralized and non-mineralized hydrogels. Error bars represent standard error of the mean (n=3) and asterisks indicate statistical significance (**:p<0.01). (B-G) Bright-field images of mesenchymal stem cells at 3d on (B) coverslips (C) mineralized hydrogels and (D) non-mineralized hydrogels, and at 14d on (E) coverslips (F) mineralized hydrogels and (G) non-mineralized hydrogels. Scale bars represent 200 μm.
Figure 12:
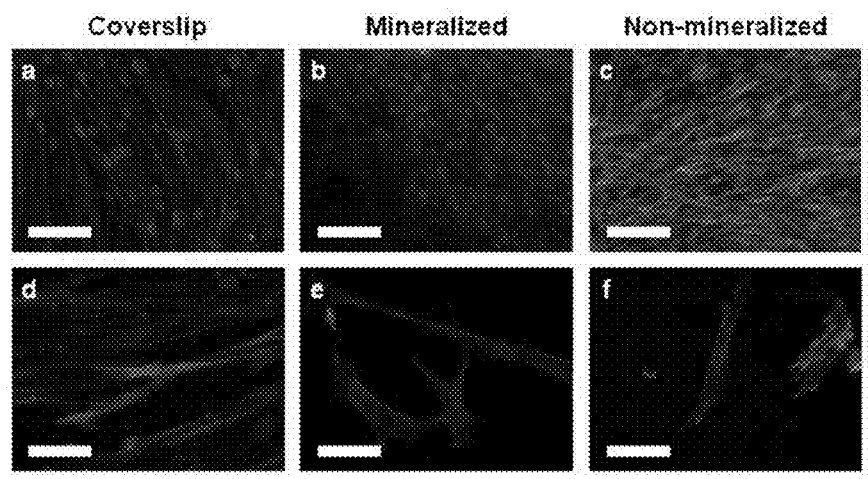
FIGS. 12A-F show pictures of (A) Staining for actin cytoskeleton in mesenchymal stem cells on (A,D) coverslips, (B,D) mineralized hydrogels (C,F) non-mineralized hydrogels at 2 weeks in growth medium. Actin is stained green, nuclei are stained blue. Scale bars represent (A-C) 100 μm and (D-F) 50 μm.
Figure 13A:
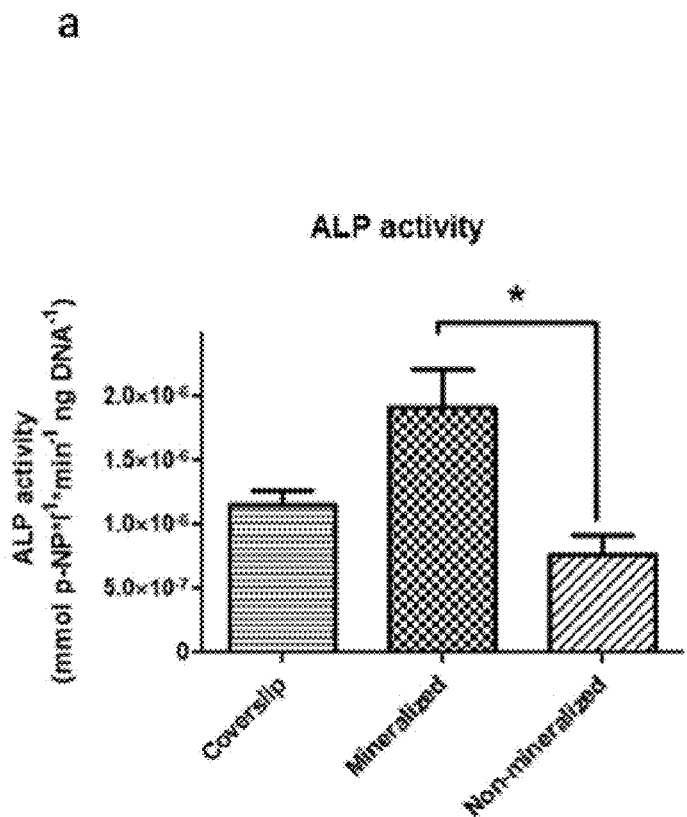

Cell attachment. Cells were found to attach to both, mineralized and non-mineralized A6ACA hydrogels and showed similar levels of proliferation with cell culture coverslips (FIG. 11A). Cells attached to all three surfaces (mineralized hydrogels, non-mineralized hydrogels and coverslips) showed similar elongated morphology with a shape index of 0.2±0.1. (FIGS. 11B-D). However, with increased culture time, significant differences were observed in cell density to the mineralized and non-mineralized hydrogels. Cells on non-mineralized hydrogels and coverslips reached 100% confluence and formed a confluent layer on the surface (FIGS. 11E,G). On mineralized hydrogels however, cells showed significantly different behavior. Upon reaching confluence, cells formed highly condensed regions. F-actin staining revealed differences in the alignment of stress fibers on mineralized and non-mineralized hydrogels and coverslips. Cells achieved 100% confluence on coverslips and non-mineralized controls and showed aligned, large stress fibers between adjacent cells that spanned the entire cell (FIGS. 12A, C, D, F). On mineralized hydrogels, the cytoskeleton appeared to contain thinner, shorter stress fibers as compared to non-mineralized hydrogels and coverslip controls; additionally the stress fibers appeared to be more prominent at the cell periphery (FIGS. 12B, E). Such cytoskeletal re-ordering of stress fibers has been previously reported during the osteogenic differentiation of hMSCs using traditional medium stimuli, suggesting that the mineralized hydrogels could promote osteogenesis of hMSCs.

Figure 14C:
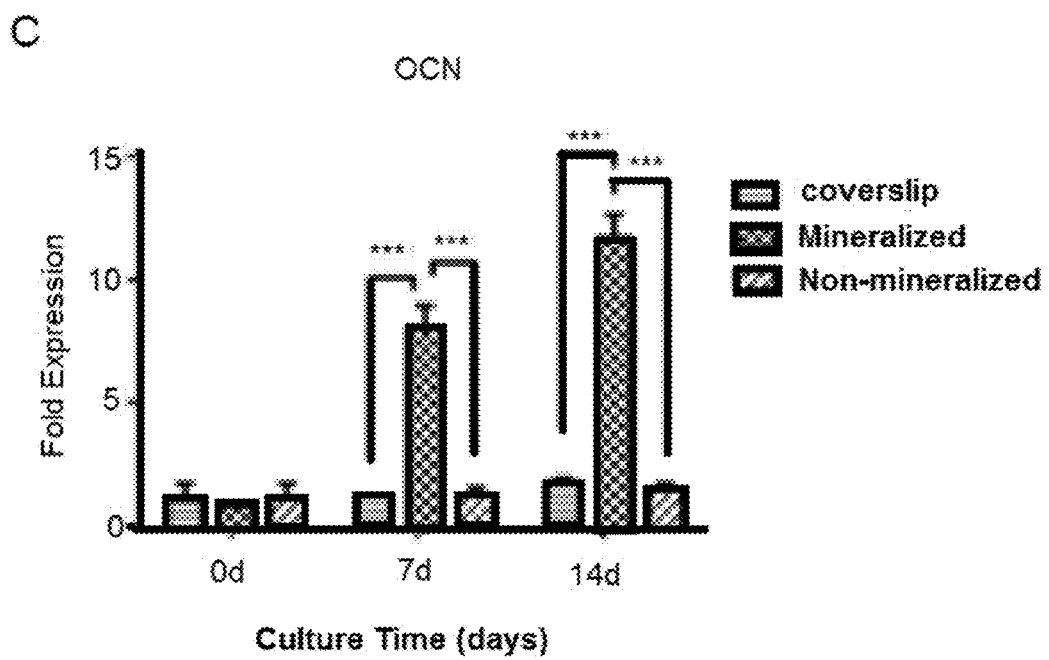

Osteogenic differentiation. Evidence for osteogenic differentiation on the mineralized hydrogels was obtained through quantitative measurement of alkaline phosphatase activity (ALP) on mineralized hydrogels, non-mineralized hydrogels and coverslips, as ALP is an early marker of osteogenesis. Mineralized hydrogels showed higher ALP activity than the other two surfaces (FIG. 13A); moreover, it is important to note that the mineralized hydrogels likely contained increased levels of inorganic phosphate which could inhibit ALP activity. The actual ALP production on mineralized hydrogels is thus likely even higher than the measured activity. Further, immunofluorescent staining for osteocalcin revealed the production of osteocalcin (OCN) in hMSCs on mineralized and non-mineralized samples, but with brighter staining in the mineralized samples (FIGS. 13B-G). Osteocalcin was first visible at 2 weeks of culture and persisted at 3 weeks. For cells seeded on coverslips and non-mineralized hydrogels, no visible staining was observed at 2 weeks, while extremely weak staining was observed at 3 weeks. Cells on mineralized hydrogels however, showed the presence of osteocalcin at 2 weeks with extremely intense staining after 3 weeks. Quantitative RT-PCR revealed the upregulation of osteogenic genes, namely Runx2, osteocalcin (OCN) and bone sialoprotein (BSP) in mineralized samples, as compared to non-mineralized hydrogels as well as coverslip controls (FIG. 14) after 14 days of culture. OCN showed upregulation at both 7 and 14 days of culture while Runx2 and BSP showed upregulation at 14 days of culture. OCN and BSP are highly specific to the osteoblastic phenotype and are associated with the production of mineralized matrix by osteoblasts; their increased expression indicates osteogenic differentiation on the mineralized hydrogels. Runx2 on the other hand, is a transcription factor that serves as a marker for early osteogenesis.

The reason behind the apparent osteoinductivity of the mineralized hydrogels was examined. The effect of differences in cell density due to differences in initial attachment to mineralized and non-mineralized hydrogels was examined, as this has been previously demonstrated to affect differentiation of MSCs. Interestingly, McBeath et al. demonstrated that lower cell densities are more conducive to osteogenic differentiation of MSCs; as observed from FIG. 11A, mineralized hydrogels showed similar DNA content to non-mineralized hydrogels and coverslips thus suggesting that differences in initial cell density are unlikely to have played a role in the osteogenesis of hMSCs on mineralized scaffolds. Matrix stiffness was also considered as a causative factor; due to the presence of the inorganic mineralized phase, mineralized samples are expected to show higher stiffness than non-mineralized hydrogels and increased in matrix stiffness have been demonstrated to promote osteogenesis. However, comparison of hMSCs seeded on mineralized samples with those seeded on coverslips showed that mineralized A6ACA hydrogels promoted osteogenesis to a much greater extent, despite the coverslips being substantially stiffer. Moreover, the mineralized hydrogels were indeed to possess a higher compressive modulus than their non-mineralized counterparts (31 kPa for mineralized vs 17 kPa for non-mineralized) and as a result, non-mineralized hydrogels with a compressive modulus of 31 kPa were synthesized by tuning cross-link density and subsequently used as non-mineralized controls. As observed in FIG. 10D, mineralized hydrogels present a vastly different surface topography as compared to non-mineralized hydrogels; as topographical cues have been shown to promote osteogenesis of hMSCs, the rough topography presented by the mineralized hydrogels may be a factor behind their ability to promote osteogenic differentiation.

The osteogenesis of hMSCs on the mineralized samples may be caused by higher local concentration of calcium and phosphate ions on account of dissolution-reprecipitation of the calcium phosphate phase on the mineralized samples. It is currently believed that calcium phosphates are capable of dissolving to a limited degree, releasing calcium and phosphate ions. When this takes place in calcium and phosphate-saturated aqueous solutions, this release leads to spontaneous precipitation of calcium phosphate due to local increase in calcium and phosphate concentrations, in conjunction with the low solubility product of calcium phosphates at physiological pH. Due to the saturation of physiological fluids with respect to calcium phosphate, calcium phosphate minerals are also able to sequester calcium and phosphate ions from the ambient environment and nucleate additional calcium phosphates. This dissolution-reprecipitation has been previously demonstrated in bioactive ceramics and has been previously suggested as contributing to their osteoinductivity; moreover, higher levels of calcium and phosphate have been demonstrated to promote osteogenesis of progenitor cells. It was examined whether the dissolution-reprecipitation of the calcium phosphate phase took place in the mineralized hydrogels by measuring their ion release in ion-free medium, as well as by measuring their ion uptake in growth medium. The data showed that there was a release of both, $Ca^{2+}$ and $PO_4^{3-}$ ions from acellular mineralized hydrogels in ion-free 50 mM Tris (pH 7.4; FIG. 15A), which demonstrates dissolution of the mineralized phase over a period of 1 week. Moreover, the molar ratio of released $Ca^{2+}$ and $PO_4^{3-}$ was consistently approximately 1.7 which is very close to the stoichiometric Ca—P ratio in hydroxyapatite (1.67) suggesting that the $Ca^{2+}$ and $PO_4^{3-}$ release was due to dissolution of an apatite-like phase. Interestingly however, when acellular mineralized hydrogels were immersed in hMSC growth medium, a marked decrease was observed in the concentrations of both $Ca^{2+}$ and $PO_4^{3-}$ with time, suggesting additional mineralization of the scaffolds. This was supported by an observed increase in $Ca^{2+}$ content of the mineralized scaffolds with time. It is also important to note that the non-mineralized scaffolds also eventually underwent mineralization with time, as demonstrated by the increase in Ca content, albeit to a lower extent than the mineralized hydrogels. These observations suggest that while dissolution-reprecipitation likely takes place at the surface of the mineralized scaffolds, reprecipitation is the dominant process. The mechanism behind this is unclear; it is possible that the mineralized phase promoted additional precipitation of calcium phosphate from the medium. Moreover, the role of serum proteins in biomineralization has been previously established; it is possible that in serum-supplemented medium, A6ACA substrates (both mineralized and non-mineralized) adsorbed components of serum that promoted additional nucleation. The ion uptake by both, mineralized and non-mineralized hydrogels could also be due to diffusion into the hydrogel interior, followed by their subsequent nucleation to carboxyl groups in the interior of the hydrogel. The dominance of reprecipitation suggests a higher local concentration of $Ca^{2+}$ and $PO_4^{3-}$ ions at the surface of the mineralized samples; it is thus possible that the hMSCs on the mineralized scaffolds are exposed to increased concentrations of $Ca^{2+}$ and $PO_4^{3-}$ ions. Indeed, A6ACA-co-acrylamide hydrogels have been shown to promote osteogenic differentiation of hMSCs, both with and without osteogenesis-inducing supplements.

Figure 16:
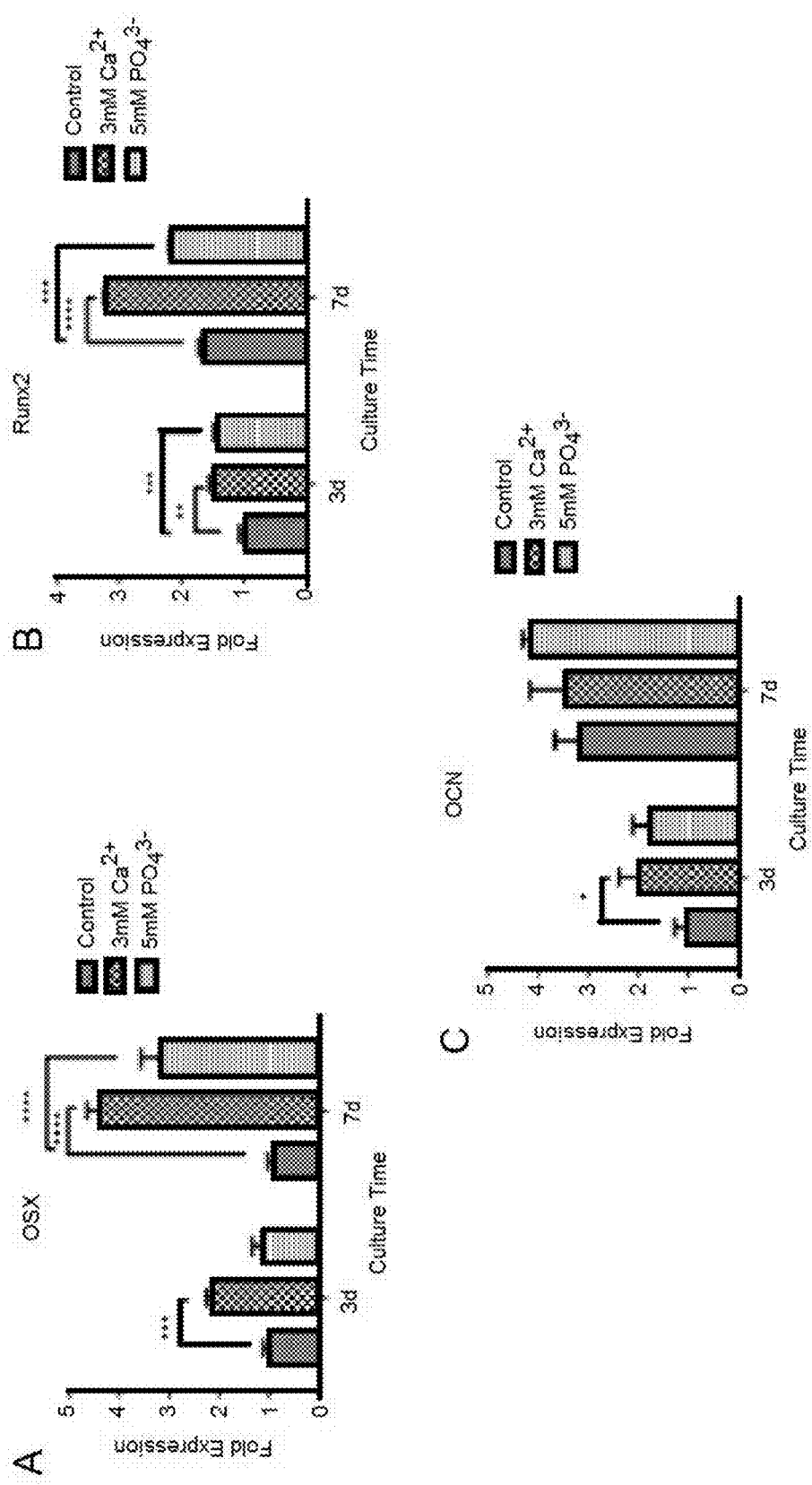
FIGS. 16A-C show expression of osteogenic markers in $Ca^{2+}$ and $PO_4^{3-}$ supplemented medium. Expression of (A) OSX (B) Runx2 (C) OCN in hMSCs cultured in control, high calcium and high phosphate media respectively, normalized to GAPDH, relative to day 3 samples cultured in control medium. Error bars represent standard error of the mean, asterisks indicate statistically significant differences from control medium (*:p<0.05, p<0.01, *: p<0.001, ****: p<0.0001).

In order to further evaluate the effect of soluble $Ca^{2+}$ and $PO_4^{3-}$ concentrations on hMSC differentiation, hMSCs seeded on TCPS were exposed to growth medium supplemented with increased levels of $Ca^{2+}$ and $PO_4^{3-}$ respectively; upregulation of OSX and RUNX2 (early markers of osteogenesis) and to a lesser extent were observed, OCN in both high-calcium and high-phosphate medium, as compared to hMSCs cultured in control growth medium (FIG. 16). The gene expression data indicates that $Ca^{2+}$-supplemented medium promoted the expression of OSX and RUNX2 to a greater extent than $PO_4^{3-}$-supplemented medium, further suggesting that release and reprecipitation of $Ca^{2+}$ and $PO_4^{3-}$ could play a role in initiating osteogenesis on the mineralized hydrogels. The data suggest that hMSCs seeded on mineralized A6ACA hydrogels were exposed to higher levels of $Ca^{2+}$ and $PO_4^{3-}$ at the material surface which then led to their subsequent osteogenesis even in the absence of dexamethasone or exogenously added β-glycerolphosphate. It is important to note that at 3 and 7 days, supplementation of the culture medium with $Ca^{2+}$ and $PO_4^{3-}$ was only able to stimulate expression of early osteogenic markers (viz. RUNX2 and OSX) and not late markers such as OCN or BSP. This is in contrast with the mineralized hydrogels, which were able to induce significant osteocalcin expression as compared to coverslip controls and non-mineralized hydrogels even at 3 and 7 days of culture. This suggests that while dynamic mineral dissolution and reprecipitation is a possible mechanism behind initiating osteogenic differentiation of hMSCs on the mineralized hydrogels, it is also likely dependent on other cues such as chemical and topographical cues from the bone-mimicking mineral.

Figure 17:
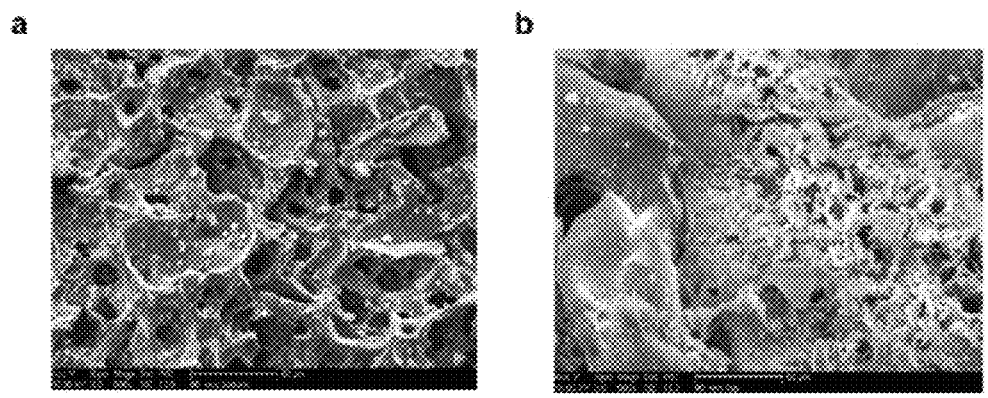
FIGS. 17A-B show data from PEGDA-A6ACA cryogels (A) nonmineralized cryogels and (B) mineralized cryogels.
Figure 18:
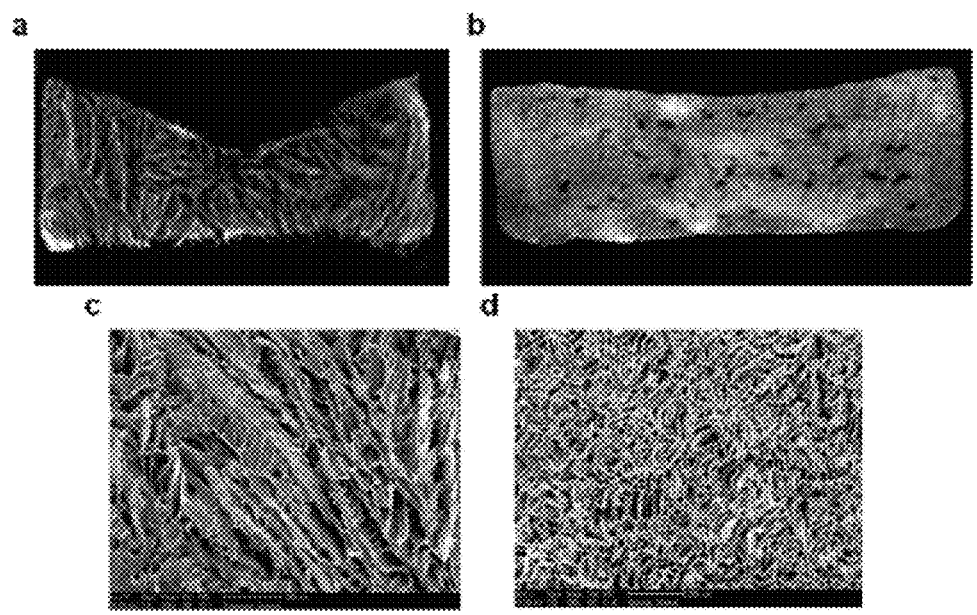
FIGS. 18A-D are images showing (A, B) MicroCT cross-sections of (A) Columnar and (B) Spongy cryogels. (C, D) SEM images of microstructure for (C) Columnar and (D) Spongy cryogels.

Three dimensional mineral/hydrogel composite scaffolds. A process to synthesize macroporous hydrogel scaffolds via gelation at −20° C. is provided, in which ice templating is used as a porogen. These hydrogels can be mineralized using the procedure detailed above and elsewhere herein. FIG. 17 shows the internal pore structure of a macroporous hydrogel (hereafter referred to as 'cryogel') and the mineralized surface of a mineralized cryogel (hereafter referred to as 'synthetic bone graft'). Additionally, by tuning the rate and direction of freezing, changes in pore size and pore structure can be performed. Using this method macroporous hydrogels were synthesized with identical composition having two pore structures: (i) large columnar pores, measuring >500 μm in diameter and (ii) smaller, dendritic pores, measuring 100-200 μm in diameter. FIG. 18 shows the different pore structures obtained, as characterized by scanning electron microscopy (SEM) and micro-computed tomography (microCT). Due to the swollen nature of hydrogels, it is not possible to obtain a microCT cross-section in their swollen state; for this, it was necessary to soak the cryogels in an $FeCl_3$ solution (to enhance contrast) and freeze-dried. However, the drying is expected to be isotropic; thus, the microstructure of the cryogels in the dried state is expected to accurate represent their microstructure in their swollen state.

In vivo response. These experiments demonstrate that in 2D culture, the synthetic bone graft material can promote osteogenesis of human mesenchymal stem cells. To explore the in vivo response of this material in the form of a three dimensional porous scaffold, cryogels were synthesized and subsequently mineralized. Three dimensional porous scaffolds were prepared from the synthetic bone graft material and implanted subcutaneously at dorsal sites in six nude rats, to determine the effect of mineralization, internal pore structure as well as the effect of pre-seeding with human mesenchymal stem cells (hMSCs). Six group were studied as outlined in Table 4, below.

TABLE 4

| Group | Pore structure | Mineralized/Non-mineralized | Seeded with hMSCs/Acellular |
|---|---|---|---|
| A | Columnar | Non-mineralized | Acellular |
| B | Columnar | Mineralized | Acellular |
| C | Spongy | Non-mineralized | Acellular |
| D | Spongy | Mineralized | Acellular |
| E | Columnar | Mineralized | Seeded with hMSCs |
| F | Spongy | Mineralized | Seeded with hMSCs |

Figure 19:
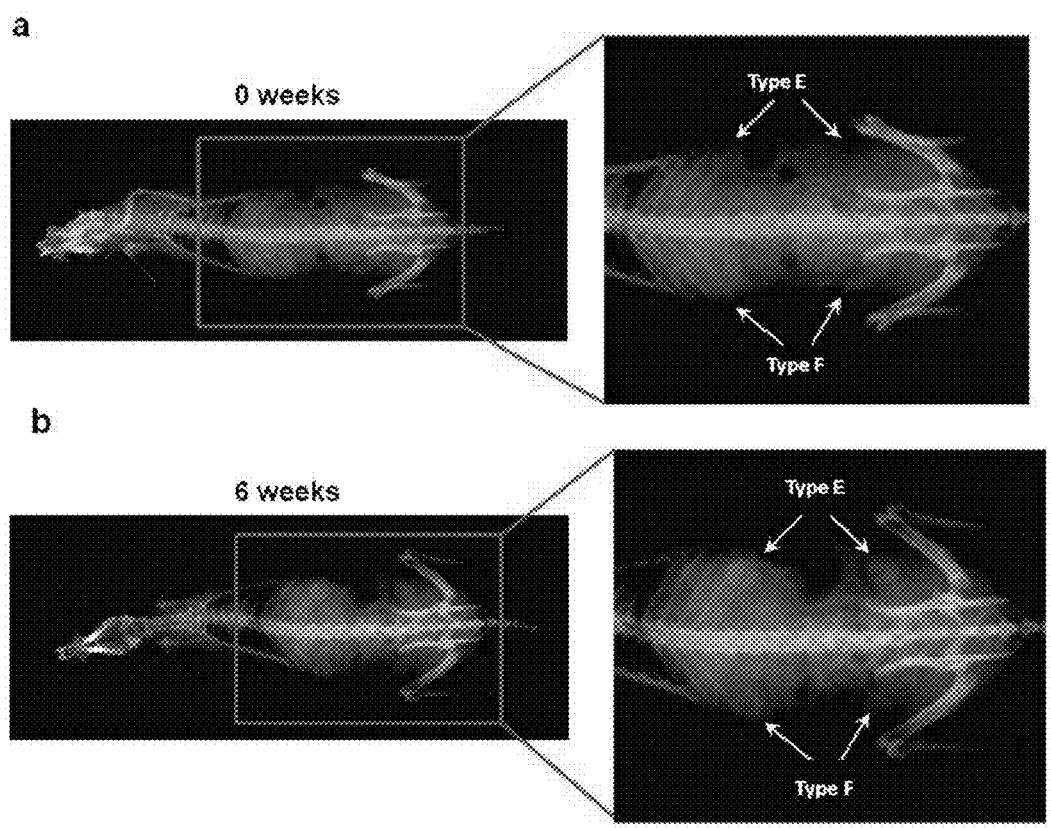
FIGS. 19A-B shows x-ray images of the same nude rat with cell-seeded mineralized grafts at (A) 0 weeks (time of implantation) and (B) 6 weeks of implantation. As observed in (B) the implants become clearly visible at 6 weeks, suggesting the formation of hard tissue post-implantation.

Animals were monitored every two weeks via Xray. At implantation, implants were not visible in the X-rays. Beginning at 4 weeks however, mineralized grafts (both acellular and hMSC seeded) were visible on the X-rays, suggesting formation of hard tissue. (see, FIG. 19). Animals were also injected with calcein as a bone label at 7 weeks. Implants were resected at 9 weeks and fixed by immersion in 4% paraformaldehyde. Initial microCT analyses show the formation of hard tissue in these implants (see, FIG. 20). No hard tissue was observed in nonmineralized grafts and as a result, no microCT scans could be obtained from the non-mineralized hydrogels. This suggests that premineralization is vital to the process of hard tissue formation. Moreover, hard tissue formation was restricted to the exterior of the implant, although the columnar grafts showed ingrowth into the cell seeded and acellular scaffolds. Additionally, mineralized implants showed positive staining for calcein (FIG. 21) suggesting additional calcification between 7 and 9 weeks. These data suggest that upon subcutaneous implantation, the mineralized bone grafts were able to induce hard tissue formation (which could be ectopic bone). Gross examination of the implants did not show formation of fibrous encapsulation. Synthesis of mineralized hydrogels could thus be a low cost, effect method to promote healing of bone defects, even in the absence of exogenously added progenitor cells.

Development and characterization of cryogels with varying pore architecture. The internal microstructure of cryogels can be controlled through various cryogelation parameters such as gelation temperature, degree of supercooling, and kinetics of polymerization. In this study, the ability to control the structure of the ice network was used to develop cryogels with unique internal pore architectures without altering their chemistry or overall porosity. Indeed, controlling the ice network structure yielded cryogels with two types of distinct pore microstructure, referred to as 'spongy' and 'columnar', (FIG. 18). As shown in FIG. 18, a directional cooling front during cryogelation promoted the growth of ice columns perpendicular to the ice-polymer solution interface, and therefore cryogels having a lamellar columnar structure with a larger pore size of approximately 50-60 μm in the dried state (corresponding to ~100-150 μm in the swollen state, as estimated through bright field microscopy) were synthesized. The pore structure consisted of several oriented lamellae of columns, connected through smaller pores (subsequently referred to as 'columnar pore structure'). On the other hand, their counterparts synthesized without preferential nucleation sites (in spongy molds) led to a macroporous network consisting of more randomly oriented, interconnected cellular pores measuring approximately 20-30 μm in diameter in the dried state (corresponding to 50-60 μm in the swollen state, as estimated via bright field microscopy) throughout the constructs as shown in FIG. 18; the pore network lacked any particular orientation and will subsequently be referred to as 'spongy' pore structure. Between the two structures, the spongy cryogels showed a substantially higher pore area ($0.37\pm0.18$ $m^2/g$) than columnar cryogels ($0.17\pm0.05$ $m^2/g$) (Table 5). Interestingly, despite the vast difference in pore shape and size, mercury intrusion porosimetry suggested similar porosity between the spongy and columnar cryogels; spongy cryogels had a porosity of $70.0\pm0.4\%$ while columnar cryogels had a porosity of $70\pm5\%$. Porosity measurements for columnar cryogels were further supported through analysis of the microCT reconstructions which suggested a porosity of 67% for columnar constructs; the small size of pores in the lyophilized spongy cryogels coupled with insufficient resolution of the scanner did not allow for their accurate porosity quantification through microCT.

TABLE 5

| Properties | Unit | Spongy | Columnar |
|---|---|---|---|
| Total Pore Area | m²/g | 0.37 ± 0.18 | 0.17 ± 0.05 |
| Median Pore Diameter (Volume) | μm | 28.27 ± 11.99 | 60.07 ± 16.36 |
| Median Pore Diameter (Area) | μm | 19.27 ± 6.88 | 30.37 ± 7.75 |
| Average Pore Diameter (4 V/A) | μm | 26.69 ± 10.59 | 45.56 ± 9.93 |
| Porosity | % | 70.0 ± 0.4 | 70 ± 5 |

Effect of pore structure on osteogenic differentiation of hMSCs in vitro. Following 24 hours of culture in growth medium, cells showed similar viability (>90%) in both spongy and columnar cryogels. A notable difference between the two cryogels, however, was the difference in morphology of the cells within the cryogels. Cells cultured in spongy cryogels showed a more spread morphology, compared to cells seeded in columnar cryogels which formed small cellular aggregates along the pore walls. DNA quantification at 7 and 21 days demonstrated proliferation of cells between 0 and 7 days (approximately 1.5-fold), with both cryogels showing similar DNA content. However, no significant proliferation was observed between 7 and 21 days. Spongy cryogels showed a slight decrease in cell content with culture time though the decrease was not statistically significant. The similar DNA content after 21 days suggests similar cell proliferation between the spongy and columnar cryogels.

Gene expression analyses suggested that both the cryogels supported osteogenic differentiation of the hMSCs compared to day 0 controls, as evidenced by the upregulation of the osteogenic markers Runx2, OCN, and OPN throughout the culture period. However, there were significant differences in the temporal expression levels depending upon the type of cryogel microstructure. Specifically, cells in spongy cryogels showed significantly higher upregulation of Runx2 at 4 days of culture, OPN at 14 days of culture and OCN at 21 days of culture, as compared to columnar cryogels. This suggests that the spongy cryogels promoted osteogenic differentiation at a more rapid pace than the columnar cryogels.

The extent of osteogenesis in the cryogels was additionally measured by quantifying the activity of alkaline phosphatase, as well as the cell-mediated calcification. Indeed, spongy cryogels showed substantially higher ALP activity than columnar cryogels at all time points, up to 21 days of culture. Additionally, spongy cryogels showed higher calcium content, although the difference was not statistically significant. Given the similar DNA content of spongy and columnar cryogels throughout the study, this suggests that the spongy cryogels were more conducive to osteogenic differentiation than the columnar cryogels. Immunofluorescent staining also revealed the presence of OCN in hMSCs cultured in both spongy and columnar cryogels, providing further evidence that these cryogels supported osteogenic differentiation.

Figure 20:
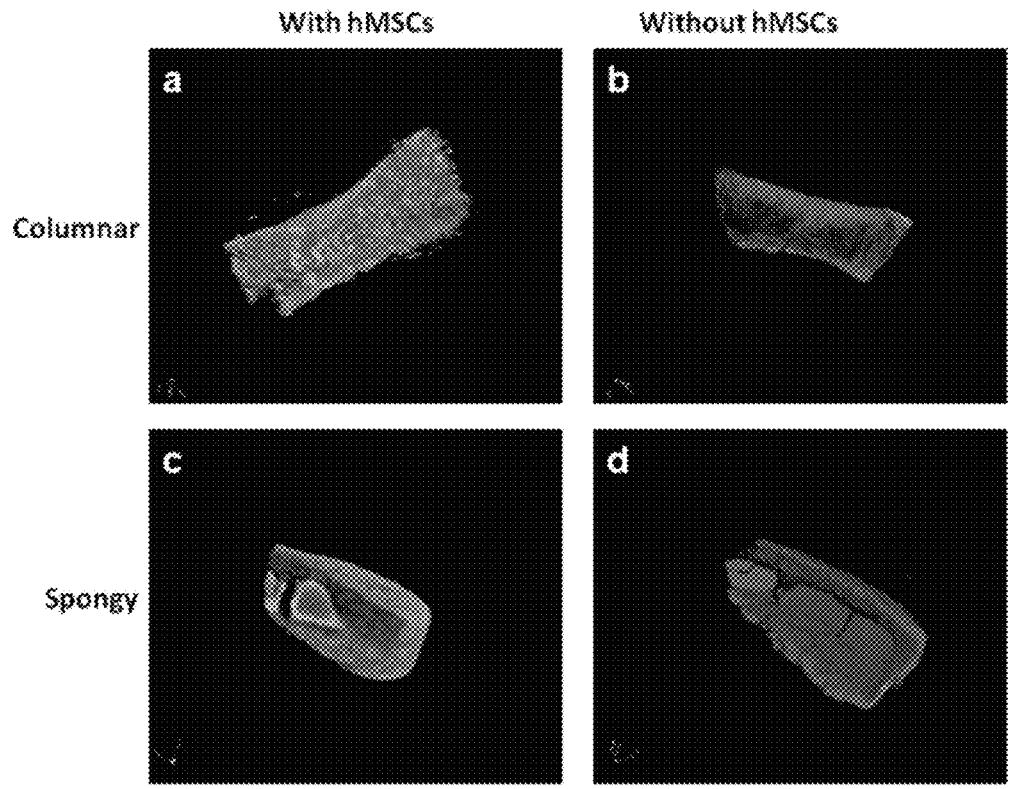
FIGS. 20A-D shows 3D reconstructions of resected mineralized cryogels (A, C) seeded with hMSCs and (B, D) without hMSC pre-seeding.
Figure 21:
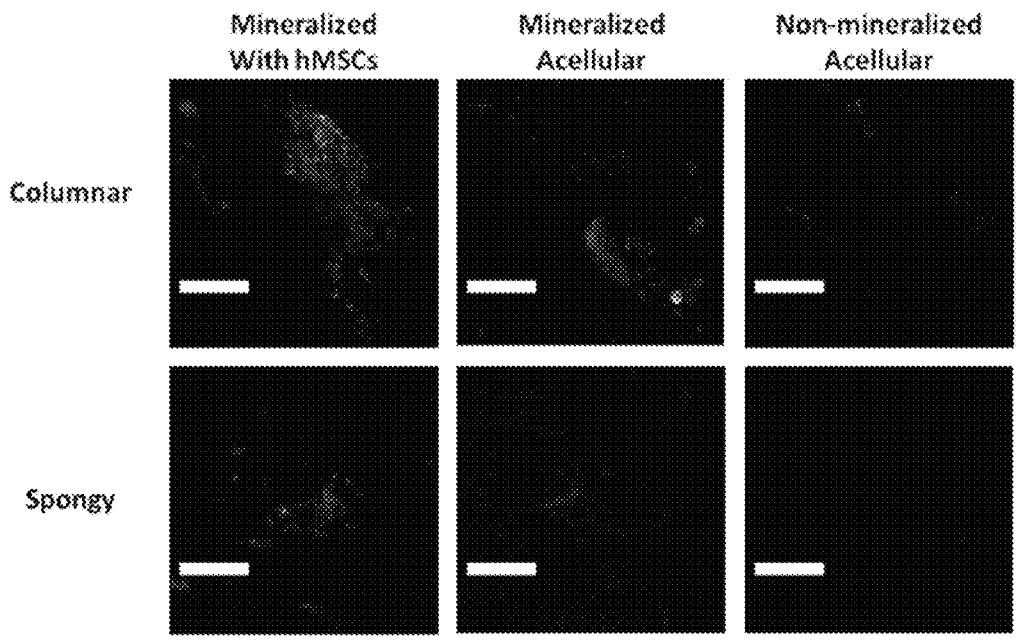
FIG. 21 show panels of confocal fluorescence images of explanted grafts from various groups, showing positive staining for Calcein at week 7, indicating post-week 7 calcification.
Figure 22:
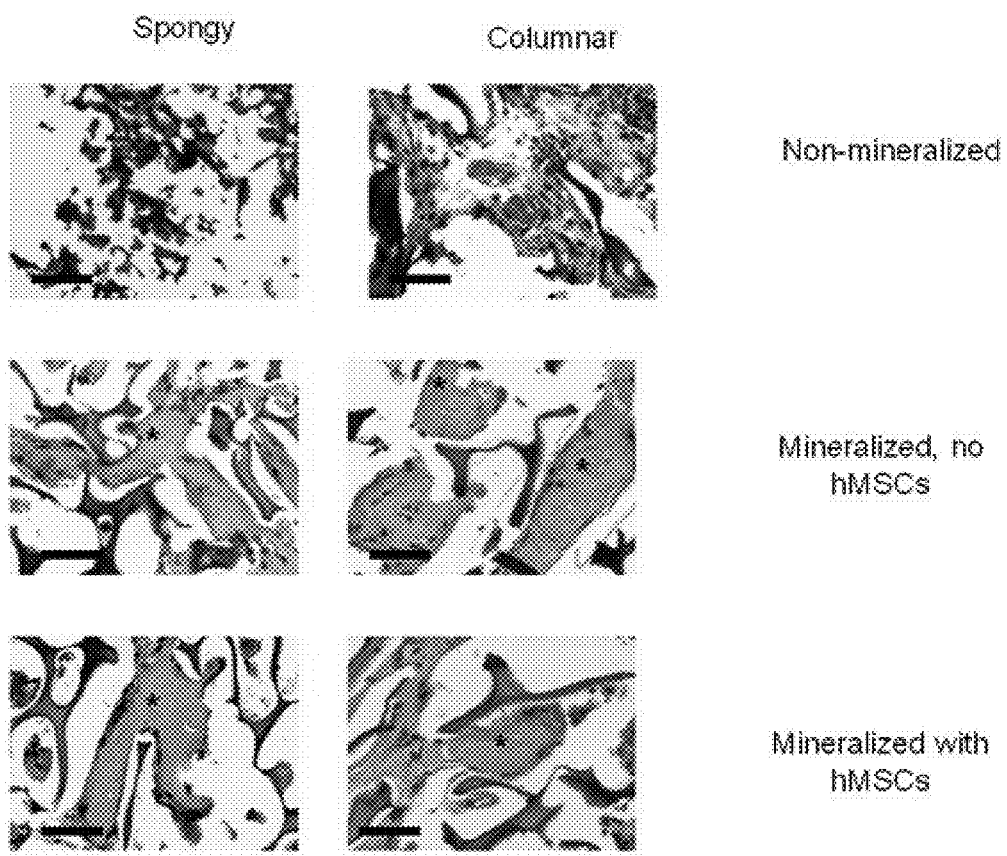
FIG. 22 show histology images of cryogels implanted subcutaneously in nude rats for 9 weeks. '*' indicates new bone formation. Scale bars represent 50 μm.
Figure 23:
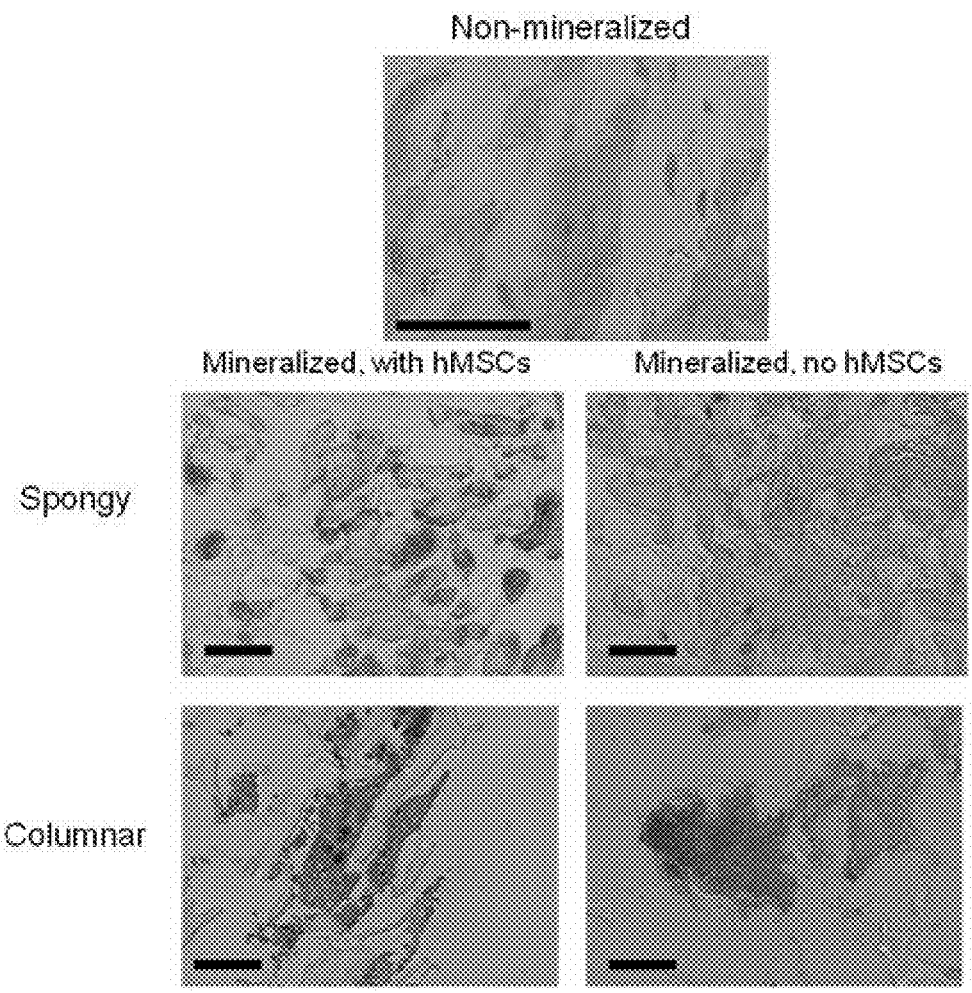
FIG. 23 shows immunohistochemical staining for the bone marker osteocalcin in the cryogels implanted subcutaneously in nude rats. Dark stain indicates positive staining for osteocalcin. Scale bars represent 100 μm.

In vivo tissue formation. The ability of mineralized PEG-A6ACA hydrogels to induce osteogenic differentiation of hMSCs even in the absence of osteogenic inducing soluble factors and growth factors employing a 2D culture condition was described above. Thus, the in vivo subcutaneous response to mineralized and non-mineralized cryogels in a nude rat model was analyzed. First, the mineralization of the cryogels was confirmed through scanning electron microscopy and elemental analysis. Elemental analysis revealed a Ca/P ratio of 1.7, suggesting the presence of an apatite-like mineralized phase. Next, the ability of the implanted cryogels to promote bone tissue formation was evaluated by using a number of different acellular and cellular cryogels. These include (i) acellular columnar cryogels (non-mineralized), (ii) acellular spongy cryogels (non-mineralized), (iii) acellular columnar cryogels (mineralized), (iv) acellular spongy cryogels (mineralized), (v) hMSC-seeded columnar cryogels (mineralized) and (vi) hMSC-seeded spongy cryogels (mineralized). After 9 weeks of implantation, all mineralized cryogels (groups iii-vi) showed evidence of hard tissue formation, irrespective of pore structure or seeding with hMSCs prior to implantation. All mineralized cryogels showed the formation of peripheral hard tissue, as observed through micro-computed tomography and radiographs (FIGS. 20, 24C). Gross examination post-excision from implantation sites also revealed infiltration of host cells into the mineralized cryogels. Histological analysis revealed the formation of bone-like tissue in the hard tissue layer, accompanied by the in-growth of host vasculature into the scaffold, suggesting that the mineralization of the cryogels played a crucial role in the vascularization and bone formation in the cryogels (FIG. 22). Additionally, the hard tissue layer showed presence of OCN as evidenced by immunohistochemical staining, further suggesting that the mineralized cryogels promoted bone formation in vivo (FIG. 23). It is important to note that the presence of the mineral layer was expected to reduce the effective size of the pores. Mercury intrusion porosimetry revealed that mineralization only reduced average pore diameter by approximately 2 μm, suggesting that mineralization was unlikely to restrict access into construct interior through pore closure.

Non-mineralized cryogels (groups i-ii), on the other hand showed a dramatically different response from their mineralized counterparts. Unlike the mineralized cryogels, no hard tissue formation was observed even at 9 weeks of implantation for non-mineralized cryogels, supported through lack of hard tissue detection in micro-CT. Moreover, unlike the mineralized cryogels, the pore architecture was seen to play a major role in host cell infiltration into the non-mineralized cryogels. Non-mineralized cryogels with spongy pore architecture showed negligible host cell infiltration, as observed through gross examination as well as histological analyses (FIG. 22). Non-mineralized columnar cryogels on the other hand, showed host cell infiltration, but with abundant fibrous tissue and extensive vascularization in the scaffold interior, without any bone information as indicated by the lack of OCN staining (FIG. 23). The histology, lack of hard tissue formation and immunohistochemical analyses suggested that the non-mineralized columnar cryogels did not promote bone formation in vivo.

The experiments demonstrate that during freezing of aqueous solutions, the morphology of the ice network is governed by the directionality of the cooling front and the solid-liquid interface between the solid ice and liquid aqueous solution, both of which control the directionality of the ice network. By manipulating the directionality of ice crystal formation by controlling the directionality of the cooling front and the solid-liquid interface (between the solid ice and the liquid polymer precursor solution) the internal pore architecture of the cryogel scaffolds was modified. To create the directionality of internal pore structures, a thin ice layer was introduced at the bottom of the mold to provide preferential nucleation sites, allowing for columnar ice dendrite growth without changing the precursor composition. The underlying ice layer provides a more drastic temperature gradient within the polymerizing solution from top to the bottom in the columnar molds than their spongy counterparts which have the exact same precursor composition but a more uniform, isotropic temperature gradient as they lack the pre-formed ice layer. In the case of the columnar cryogels, the presence of ice layer in the bottom of the mold prior to polymerization leads to a cooling front which advances growth of ice crystal perpendicular to the solid-liquid interfaces (uni-directionally upward from the bottom of the mold). This ice bed provides a template from which dendritic ice crystals grow in a lamellar fashion. This lamellar, oriented ice network provides directionally oriented lamellar, columnar pores upon thawing of the network. Spongy cryogels were prepared using isotropic cooling which led to randomly oriented, cellular pores. This led to the formation of an isotropic ice network that did not favor any particular orientation, and therefore resulted in an isotropic pore network. Indeed, a previous study reported the simultaneous presence of a columnar-like pore zone and spongy-like cellular pore zone during the freeze-casting of hydroxyapatite through manipulation of the freezing front morphology and the freezing kinetics (Deville et al., 2006). The disclosure demonstrates the formation of synthetic polymeric scaffolds with distinctly different microarchitecture mimicking different structural attributes of bone tissues. Such scaffold could be a tool to gain insight into the effect of pore microarchitecture on cellular functions in vitro and in vivo.

It is possible that spongy and columnar cryogels promoted differential transport of nutrients and waste products due to their differing microstructure and the interconnectedness of the pores, leading to the observed difference during in vitro osteogenesis of hMSCs on these cryogels. Another possible factor is the cell shape; hMSCs seeded in spongy cryogels appeared to assume spread morphology over the cryogel pore surface, while hMSCs in columnar cryogels formed aggregates with roughly a spherical morphology in the pores without significant spreading. As spread morphology has been previously demonstrated to favor osteogenesis of hMSCs, this could be another factor favoring osteogenic differentiation in the spongy cryogels. It is important to note that while spongy cryogels promoted enhanced osteogenic differentiation of hMSCs, columnar scaffolds supported their osteogenic differentiation as well, albeit at a slower pace.

The disclosure also demonstrates that spongy and columnar cryogels could promote bone formation in vivo. The formation of ectopic bone tissue in all mineralized cryogels, irrespective of pore architecture and the presence/absence of hMSCs suggest that the presence of the mineralized phase led to recruitment of endogenous progenitors from the surrounding host tissue. It is likely that the formation of bone tissue was stimulated through a variety of cues arising from the mineralized matrix, such as topographical cues as well as chemical cues arising from the dynamic dissolution-reprecipitation of the mineralized phase, suggested as mechanisms underlying the osteoinductive properties of calcium phosphates in ectopic bone formation studies. Intriguingly, mineralization of the cryogels was also found to promote vascularization, as evidenced by the presence of vascularization in the mineralized spongy cryogels and lack of vascularization in non-mineralized spongy cryogels. This is in agreement with a previous study that demonstrated improved angiogenesis in polymer-ceramic composites, when compared to pure polymeric scaffolds. This pro-angiogenic effect could be due to a variety of reasons. One potential mechanism underlying this pro-angiogenic behavior is enhanced adsorption of proteins including endogenous pro-angiogenic factors such as VEGF by the mineralized phase, leading to their concentration in the implant (Lee et al., 2011). Calcium-containing bioactive glasses have also been demonstrated to stimulate the release of pro-angiogenic factors such as VEGF from fibroblasts in vitro; a similar effect in vivo could be another reason behind the improved vascularization of the mineralized cryogels.

The differential host cell infiltration into the non-mineralized spongy and columnar cryogels could be attributed to the difference in pore size between the cryogels. A recent study demonstrated that a pore size of 100 μm-150 μm is more conducive to host cell infiltration into macroporous hydrogel scaffolds than a pore size of 25 μm-50 μm; similarly in this study, the large pore size of the columnar PEGDA-co-A6ACA cryogels (100-150 μm) was thus likely more conducive to vascular in-growth than the relatively smaller pore size (50-60 μm) of the spongy cryogels, resulting in extensive host cell infiltration and vascularization of the former but not the latter. However, the bioactivity imparted by the presence of the mineral layer was sufficient to overcome this issue, as evidenced by the vascularization and host cell infiltration into the mineralized spongy cryogels, in stark contrast with the lack of host cell penetration observed in the non-mineralized spongy cryogels.

Figure 24:
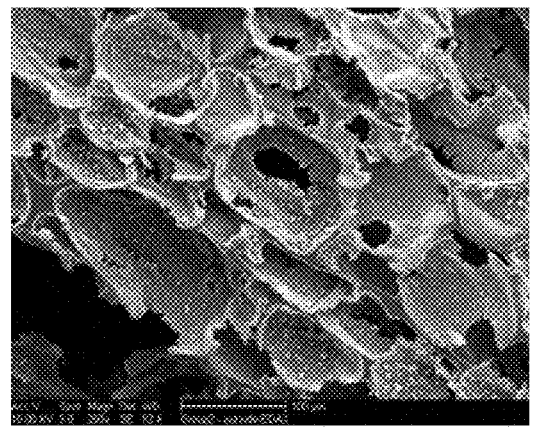
FIG. 24 shows the porous hydrogel synthesized through leaching of components (such as PMMA beads) and subsequently mineralized.

In addition to using cryogelation, porous hydrogel scaffolds were utilized by leaching of poly(methylmethacrylate) (PMMA) microspheres with an average diameter of 165 μm. Briefly, the microspheres were sintered together at 145° C. to form a bead cake. A precursor solution (in 0.5 M NaOH) of 20% PEGDA3.4K, 9.25% A6ACA, 0.5% APS, 0.08% TEMED was vacuum-infiltrated into this bead cake and allowed to polymerize at 37° C. The PMMA bead cake was then removed through washing in acetone, leading to the formation of spherical pores and was then subsequently mineralized as described for cryogels (FIG. 24). The scaffolds were cut into pieces and then implanted in a posterolateral fusion nude rat model (0.4 g/side in each animal), leading to formation of a bony fusion mass at 4 weeks without addition of any exogenous osteoinductive growth factors (FIG. 25), providing further evidence of the intrinsic osteoinductivity of the material.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising a hydrogel modified with amino acids having an anionic pendant side chain and having the general formula $CH_2$=$CHCONH(CH_2)_n COOH$, where n=1 to 12.

2. The composition of claim 1, wherein the hydrogel comprises amino acids selected from the group consisting of:
(a) $CH_2$=$CHCONH(CH_2)COOH$,
(b) $CH_2$=$CHCONH(CH_2)_2 COOH$,
(c) $CH_2$=$CHCONH(CH_2)_3 COOH$,
(d) $CH_2$=$CHCONH(CH_2)_4 COOH$, and
(e) any combination of (a)-(d).

3. The composition of claim 1, wherein the composition is mineralized.

4. The composition of claim 1, wherein the composition comprises $CH_2$=$CHCONH(CH_2)_3 COOH$.

5. The composition of claim 1, wherein the composition is seeded with cells.

6. The composition of claim 5, wherein the cells are stromal cells.

7. The composition of claim 6, wherein the stromal cells are selected from fibroblast cells, chondrocytes, osteocytes and a combination thereof.

8. The composition of claim 5, wherein the cells are stem cells.

9. The composition of claim 8, wherein the stem cells are mesenchymal stem cells.

10. The composition of claim 5, wherein cells are selected from the group consisting of endothelial cells, myoblasts, cardiomyocytes, stem cells, skeletal muscle cells, smooth muscle cells, fibroblasts, a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multipotent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell.

11. The composition of claim 1, wherein the hydrogel is molded.

12. The composition of claim 1, wherein the hydrogel is composed of a material selected from the group consisting of agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol) mono methacrylate, chitin, poly(hydroxyalkyl methacrylate), poly (electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester cross-linked polyglucans, and derivatives and combinations thereof.

13. The composition of claim 1, further comprising serum proteins.

14. A macroporous composition comprising amino acids having an anionic pendant side chain and having the general formula $CH_2$=$CHCONH(CH_2)_n COOH$, where n=1 to 8.

15. The macroporous composition of claim 14, wherein the macroporous composition comprises amino acids having a general formula selected from the group consisting of:
(a) $CH_2$=$CHCONH(CH_2)COOH$,
(b) $CH_2$=$CHCONH(CH_2)_2 COOH$, (c) $CH_2=CHCONH(CH_2)_3COOH$,
(d) $CH_2=CHCONH(CH_2)_4COOH$, and
(e) any combination of (a)-(d).

16. The macroporous composition of claim 14, wherein the composition is mineralized.

17. The macroporous composition of claim 14, wherein the composition comprises $CH_2=CHCONH(CH_2)_3COOH$.

18. The macroporous composition of claim 14 having a lamellar columnar structure with a pore size of approximately 50-60 μm in the dried state (corresponding to ~100-150 μm in the swollen state) and comprising an acryloyl amino acid selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof.

19. A macroporous composition of claim 14, comprising randomly oriented, interconnected cellular pores measuring approximately 20-30 μm in diameter in the dried state (corresponding to 50-60 μm in the swollen state) and comprising an acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof.

20. A macroporous composition of claim 14, comprising spherical interconnected pores 200-300 μm in diameter and comprising an acryloyl amino acids selected from the group consisting of $CH_2=CHCONH(CH_2)COOH$, $CH_2=CHCONH(CH_2)_2COOH$, $CH_2=CHCONH(CH_2)_3COOH$, $CH_2=CHCONH(CH_2)_4COOH$, and any combination thereof.

21. The macroporous composition of claim 14, wherein the composition is seeded with cells.

22. The macroporous composition of claim 21, wherein the cells are stromal cells.

23. The macroporous composition of claim 22, wherein the stromal cells are selected from fibroblast cells, chondrocytes, osteocytes and a combination thereof.

24. The macroporous composition of claim 21, wherein the cells are stem cells.

25. The macroporous composition of claim 24, wherein the stem cells are mesenchymal stem cells.

26. The macroporous composition of claim 21, wherein cells are selected from the group consisting of endothelial cells, myoblasts, cardiomyocytes, stem cells, skeletal muscle cells, smooth muscle cells, fibroblasts, a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a postnatal stem cell.

27. The macroporous composition of claim 14, wherein the macroporous composition is molded.

28. The macroporous composition of claim 14, wherein the macroporous composition is composed of a material selected from the group consisting of agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol) monomethacrylate, chitin, poly(hydroxyalkyl methacrylate), poly(electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester cross-linked polyglucans, and derivatives and combinations thereof.

29. The macroporous composition of claim 14, wherein the macroporous composition is formed through cryogelation or through PMMA-microsphere leaching, gas-foaming or salt leaching.

30. A method of treating a bone disease or disorder comprising a hydrogel of claim 1 in a subject at the site of desired bone formation.

31. A method of growing bone tissue comprising culturing a hydrogel of claim 5, under conditions for formation of bone tissue.

32. A method of treating a bone disease or disorder comprising a macroporous composition of claim 14 in a subject at the site of desired bone formation.

33. A method of growing bone tissue comprising culturing a macroporous composition of claim 21, under conditions for formation of bone tissue.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: GAPDH Forward primer

<400> SEQUENCE: 1

-continued

```
catcaagaag gtggtgaagc                                               20

<210> SEQ ID NO 2
<211> LENGTH: 22
<212> TYPE: DNA
<213> ORGANISM: Artificial Sequence
<220> FEATURE:
<223> OTHER INFORMATION: GAPDH Reverse Primer

<400> SEQUENCE: 2
gttgtcatac caggaaatga gc                                            22

<210> SEQ ID NO 3
<211> LENGTH: 16
<212> TYPE: DNA
<213> ORGANISM: Artificial Sequence
<220> FEATURE:
<223> OTHER INFORMATION: OCN Forward Primer

<400> SEQUENCE: 3
gaagcccagc ggtgca                                                   16

<210> SEQ ID NO 4
<211> LENGTH: 19
<212> TYPE: DNA
<213> ORGANISM: Artificial Sequence
<220> FEATURE:
<223> OTHER INFORMATION: OCN Reverse Primer

<400> SEQUENCE: 4
cactacctcg ctgccctcc                                                19

<210> SEQ ID NO 5
<211> LENGTH: 20
<212> TYPE: DNA
<213> ORGANISM: Artificial Sequence
<220> FEATURE:
<223> OTHER INFORMATION: RUNX2 Forward Primer

<400> SEQUENCE: 5
ccacccggcc gaactggtcc                                               20

<210> SEQ ID NO 6
<211> LENGTH: 21
<212> TYPE: DNA
<213> ORGANISM: Artificial Sequence
<220> FEATURE:
<223> OTHER INFORMATION: RUNX2 Reverse Primer

<400> SEQUENCE: 6
cctcgtccgc tccggcccac a                                             21

<210> SEQ ID NO 7
<211> LENGTH: 22
<212> TYPE: DNA
<213> ORGANISM: Artificial Sequence
<220> FEATURE:
<223> OTHER INFORMATION: BSP Forward Primer

<400> SEQUENCE: 7
aatgaaaacg aagaaagcga ag                                            22

<210> SEQ ID NO 8
<211> LENGTH: 22
<212> TYPE: DNA
<213> ORGANISM: Artificial Sequence
<220> FEATURE:
```

-continued

```
<223> OTHER INFORMATION: BSP Reverse Primer

<400> SEQUENCE: 8
atcatagcca tcgtagcctt gt                                              22

<210> SEQ ID NO 9
<211> LENGTH: 18
<212> TYPE: DNA
<213> ORGANISM: Artificial Sequence
<220> FEATURE:
<223> OTHER INFORMATION: OSX Forward Primer

<400> SEQUENCE: 9
catctgcctg gctccttg                                                   18

<210> SEQ ID NO 10
<211> LENGTH: 18
<212> TYPE: DNA
<213> ORGANISM: Artificial Sequence
<220> FEATURE:
<223> OTHER INFORMATION: OSX Reverse Primer

<400> SEQUENCE: 10
caggggactg gagccata                                                   18
```